(12) United States Patent
Margherita et al.

(10) Patent No.: US 7,534,571 B2
(45) Date of Patent: May 19, 2009

(54) DIAGNOSTIC AND PROGNOSTIC COMPOUNDS AND METHOD

(75) Inventors: Mariani Margherita, Milan (IT);
Francesco Sinigaglia, Milan (IT); Paola Panina, Milan (IT)

(73) Assignee: BioXell S.p.A., Milan (IT)

( * ) Notice: Subject to any disclaimer, the term of this patent is extended or adjusted under 35 U.S.C. 154(b) by 184 days.

(21) Appl. No.: 10/548,279

(22) PCT Filed: Mar. 10, 2004

(86) PCT No.: PCT/GB2004/001020

§ 371 (c)(1),
(2), (4) Date: Sep. 7, 2005

(87) PCT Pub. No.: WO2004/081233

PCT Pub. Date: Sep. 23, 2004

(65) Prior Publication Data

US 2006/0183125 A1 Aug. 17, 2006

(30) Foreign Application Priority Data

Mar. 10, 2003 (GB) ................................. 0305478.0

(51) Int. Cl.
*G01N 33/53* (2006.01)
(52) U.S. Cl. ...................................... 435/7.1
(58) Field of Classification Search ............... None
See application file for complete search history.

(56) References Cited

FOREIGN PATENT DOCUMENTS

| CA | 2 342 376 A | 9/2002 |
|----|-------------|--------|
| WO | WO 02/08287 A | 1/2002 |
| WO | WO 02/058721 A | 8/2002 |

OTHER PUBLICATIONS

Molecular Biology Reagents/Protocols 1992, United States Biochemical Corporation, 1991, Cleveland, Ohio, pp. 218-219.*

Bouchon et al., "TREM-1 amplifies inflammation and is a crucial mediator of septic shock," *Nature*, Apr. 26, 2001, pp. 1103-1107, vol. 410, No. 6832, MacMillan Journals Ltd., London, GB.

Nathan et al., "TREM-1: A new regulator of innate immunity in sepsis syndrome," *Nature Medicine 2001*, 2001, pp. 530-532, vol. 7, No. 5, USA.

Bouchon et al., "Cutting Edge: Inflammatory Responses can be Triggered by TREM-1, A Novel Receptor Expressed on Neutrophils and Monocytes," *Journal of Immunology*, 2000, pp. 4991-4995, vol. 164, The Williams and Wilkins Co., Baltimore, US.

\* cited by examiner

*Primary Examiner*—James Martinell
(74) *Attorney, Agent, or Firm*—Foley & Lardner LLP

(57) ABSTRACT

The present invention relates to a method of diagnosing bacterial or fungal sepsis in a subject, which method comprises the step of measuring the level of TREM-1-Ligand or TREM-1-Ligand nucleic acid in a biological sample obtained from said subject. The method can involve contacting said biological sample with a compound capable of binding TREM-1-Ligand and detecting the level of TREM-1-Ligand present in the sample by observing the level of binding between said compound and TREM-1-Ligand. Compounds, compositions and kits for use in the diagnosis of bacterial or fungal sepsis are also provided.

17 Claims, 22 Drawing Sheets

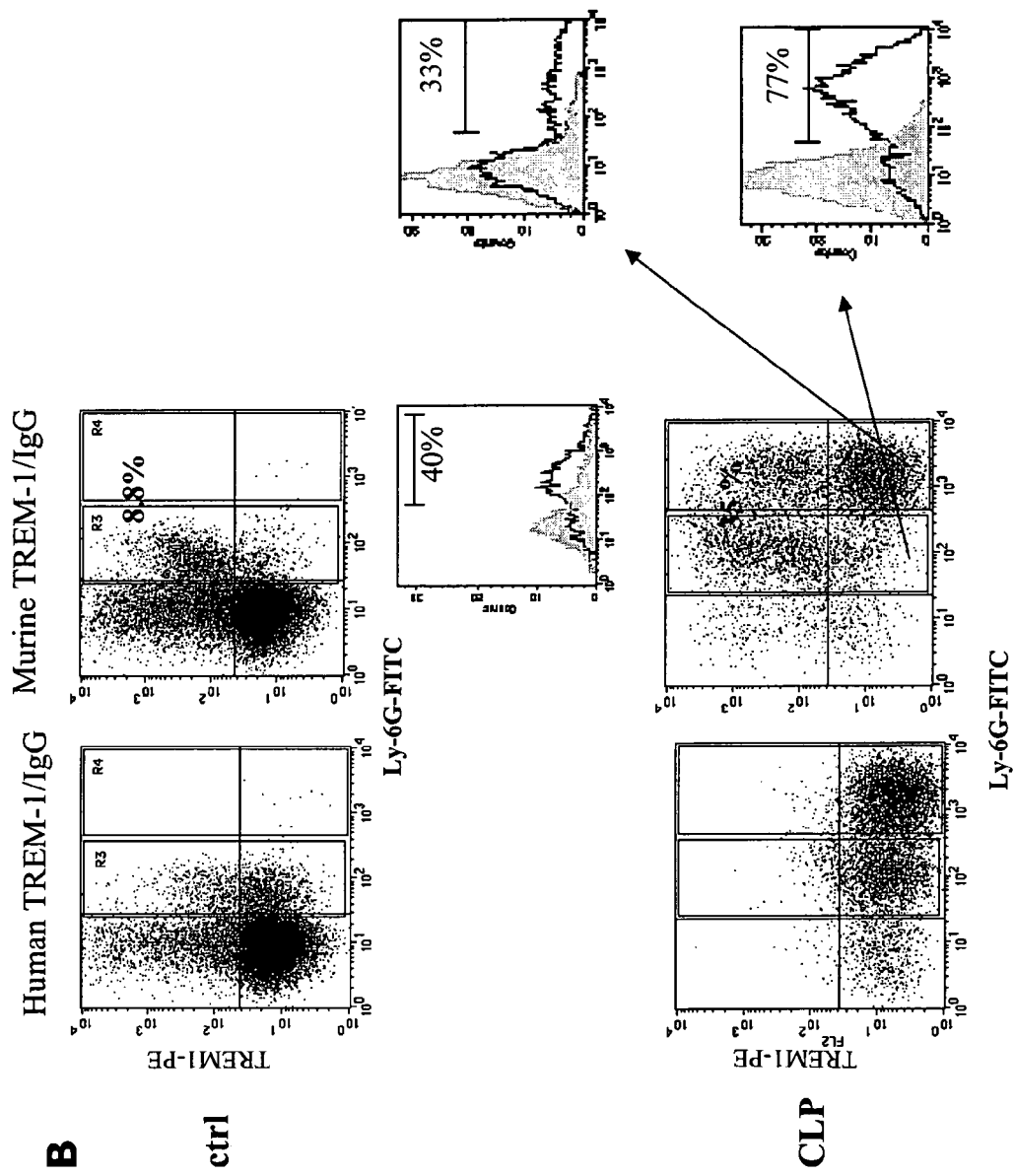
Fig. 2 – cont'd

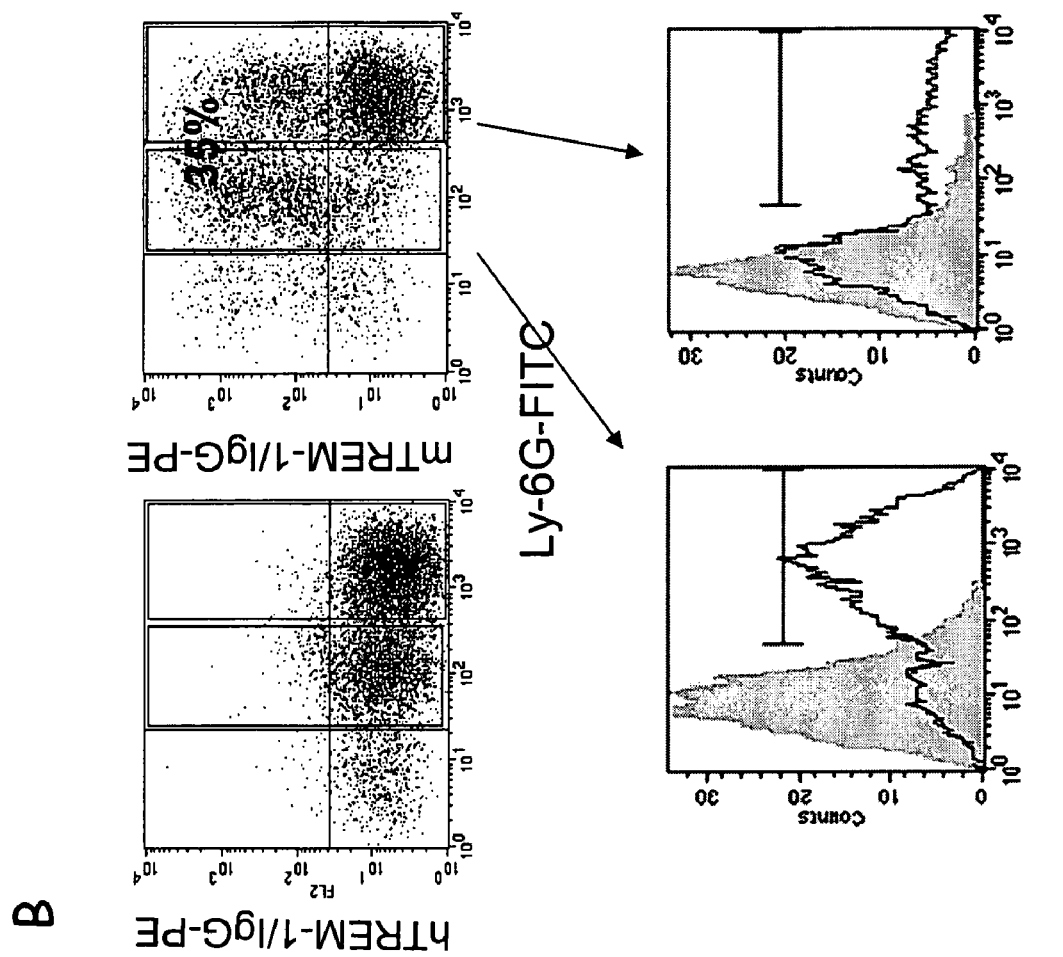
Fig. 9 – cont'd

Fig. 11

```
ctactactac taaattcgcg gccggtcgac gctggtgcac aggaaggatg aggaagacca    60
ggctctgggg gctgctgtgg atgctctttg tctcagaact ccgagctgca actaaattaa   120
ctgaggaaaa gtatgaactg aaagagggc agaccctgga tgtgaaatgt gactacacgc    180
tagagaagtt tgccagcagc cagaaagctt ggcagataat aagggacgga gagatgccca   240 agacccctggc atgcacagag aggccttcaa agaattccca tccagtccaa gtggggagga  300
tcatactaga agactaccat gatcatggtt tactgcgcgt ccgaatggtc aaccttcaag   360
tggaagattc tggactgtat cagtgtgtga tctaccagcc tcccaaggag cctcacatgc   420
tgttcgatcg catccgcttg gtggtgacca agggttttc agggacccct ggctccaatg    480
agaattctac ccagaatgtg tataagattc ctcctaccac cactaaggcc ttgtgcccac   540
tctataccag ccccagaact gtgacccaag ctccacccaa gtcaactgcc gatgtctcca   600
ctcctgactc tgaaatcaac cttacaaatg tgacagatat catcagggtt ccggtgttca   660
acattgtcat tctcctggct ggtggattcc tgagtaagag cctggtcttc tctgtcctgt   720
ttgctgtcac gctgaggtca tttgtaccct aggcccacga acccacgaga atgtcctctg   780
acttccagcc acatccatct ggcagttgtg ccaagggagg agggaggagg taaaaggcag   840
ggagttaata acatgaatta aatctgtaat caccagctat ttct            884
```

[SEQ ID NO:1] – Human TREM-1-Receptor cDNA

Fig. 12 (A)

| | | | | | | | | | | | | | | |
|---|---|---|---|---|---|---|---|---|---|---|---|---|---|---|
| Met | Arg | Lys | Thr | Arg | Leu | Trp | Gly | Leu | Leu | Trp | Met | Leu | Phe | Val | Ser |
| 1 | | | | 5 | | | | | 10 | | | | | 15 | |
| Glu | Leu | Arg | Ala | Ala | Thr | Lys | Leu | Thr | Glu | Glu | Lys | Tyr | Glu | Leu | Lys |
| | | | | 20 | | | | | 25 | | | | | 30 | |
| Glu | Gly | Gln | Thr | Leu | Asp | Val | Lys | Cys | Asp | Tyr | Thr | Leu | Glu | Lys | Phe |
| | | | | 35 | | | | | 40 | | | | | 45 | |
| Ala | Ser | Ser | Gln | Lys | Ala | Trp | Gln | Ile | Ile | Arg | Asp | Gly | Glu | Met | Pro |
| | | | | 50 | | | | | 55 | | | | | 60 | |
| Lys | Thr | Leu | Ala | Cys | Thr | Glu | Arg | Pro | Ser | Lys | Asn | Ser | His | Pro | Val |
| 65 | | | | | | 70 | | | | | 75 | | | | 80 |
| Gln | Val | Gly | Arg | Ile | Ile | Leu | Glu | Asp | Tyr | His | Asp | His | Gly | Leu | Leu |
| | | | | | 85 | | | | | 90 | | | | | 95 |
| Arg | Val | Arg | Met | Val | Asn | Leu | Gln | Val | Glu | Asp | Ser | Gly | Leu | Tyr | Gln |
| | | | | | 100 | | | | | 105 | | | | | 110 |
| Cys | Val | Ile | Tyr | Gln | Pro | Pro | Lys | Glu | Pro | His | Met | Leu | Phe | Asp | Arg |
| | | | | | 115 | | | | | 120 | | | | | 125 |
| Ile | Arg | Leu | Val | Val | Thr | Lys | Gly | Phe | Ser | Gly | Thr | Pro | Gly | Ser | Asn |
| | | | | | 130 | | | | | 135 | | | | | 140 |
| Glu | Asn | Ser | Thr | Gln | Asn | Val | Tyr | Lys | Ile | Pro | Pro | Thr | Thr | Thr | Lys |
| 145 | | | | | | 150 | | | | | 155 | | | | 160 |
| Ala | Leu | Cys | Pro | Leu | Tyr | Thr | Ser | Pro | Arg | Thr | Val | Thr | Gln | Ala | Pro |
| | | | | | 165 | | | | | 170 | | | | | 175 |
| Pro | Lys | Ser | Thr | Ala | Asp | Val | Ser | Thr | Pro | Asp | Ser | Glu | Ile | Asn | Leu |
| | | | | | 180 | | | | | 185 | | | | | 190 |

Fig. 12 (B)

```
Thr Asn Val Thr Asp Ile Ile Arg Val Pro Val Phe Asn Ile Val Ile
        195                 200                 205
Leu Leu Ala Gly Gly Phe Leu Ser Lys Ser Leu Val Phe Ser Val Leu
        210                 215                 220
Phe Ala Val Thr Leu Arg Ser Phe Val Pro
225             230
```

[SEQ ID NO:2] - Human TREM-1-Receptor amino acid sequence

Fig. 13

```
Met Arg Lys Thr Arg Leu Trp Gly Leu Leu Trp Met Leu Phe Val Ser
1           5                   10                  15
```

[SEQ ID NO:3] - Human TREM-1-Receptor (signal peptide) amino acid sequence

Fig. 14

Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
                20                  25                  30

Ala Ser Ser Gln Lys Ala Trp Gln Ile Ile Arg Asp Gly Glu Met Pro
                35                  40                  45

Lys Thr Leu Ala Cys Thr Glu Arg Pro Ser Lys Asn Ser His Pro Val
50              55                  60

Gln Val Gly Arg Ile Ile Leu Glu Asp Tyr His Asp His Gly Leu Leu
65                  70                  75                  80

Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
                100                 105                 110

Ile Arg Leu Val Val Thr Lys Gly Phe Ser Gly Thr Pro Gly Ser Asn
                115                 120                 125

Glu Asn Ser Thr Gln Asn Val Tyr Lys Ile Pro Pro Thr Thr Thr Lys
                130                 135                 140

Ala Leu Cys Pro Leu Tyr Thr Ser Pro Arg Thr Val Thr Gln Ala Pro
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg
                180         184

[SEQ ID NO:4] - Human TREM-1-Receptor (extracellular region) amino acid sequence

Fig. 15

```
Asn Ser Thr Gln
1
```

[SEQ ID NO:5] - Human TREM-1-Receptor (N-glycosylation site) amino acid sequence

```
Asn Leu Thr Asn
1
```

[SEQ ID NO:6] - Human TREM-1-Receptor (N-glycosylation site) amino acid sequence

```
Asn Val Thr Asp
1
```

[SEQ ID NO:7] - Human TREM-1-Receptor (N-glycosylation site) amino acid sequence

```
Val Pro Val Phe Asn Ile Val Ile Leu Leu Ala Gly Gly Phe Leu Ser
1               5                   10                      15

Lys Ser Leu Val Phe Ser Val Leu Phe Ala Val Thr Leu
            20              25
```

[SEQ ID NO:8] - Human TREM-1-Receptor (transmembrane region) amino acid sequence

```
Arg Ser Phe Val Pro
1               5
```

[SEQ ID NO:9] - Human TREM-1-Receptor (cytoplasmic tail) amino acid sequence

Fig. 16 (A)

```
Glu Leu Arg Ala Ala Thr Lys Leu Thr Glu Glu Lys Tyr Glu Leu Lys
1               5                   10                  15
Glu Gly Gln Thr Leu Asp Val Lys Cys Asp Tyr Thr Leu Glu Lys Phe
                20                  25                  30
Ala Ser Ser Gln Lys Ala Trp Gln Ile Ile Arg Asp Gly Glu Met Pro
            35                  40                  45
Lys Thr Leu Ala Cys Thr Glu Arg Pro Ser Lys Asn Ser His Pro Val
            50                  55                  60
Gln Val Gly Arg Ile Ile Leu Glu Asp Tyr His Asp His Gly Leu Leu
65                  70                  75                  80
Arg Val Arg Met Val Asn Leu Gln Val Glu Asp Ser Gly Leu Tyr Gln
                85                  90                  95
Cys Val Ile Tyr Gln Pro Pro Lys Glu Pro His Met Leu Phe Asp Arg
                100                 105                 110
Ile Arg Leu Val Val Thr Lys Gly Phe Ser Gly Thr Pro Gly Ser Asn
            115                 120                 125
Glu Asn Ser Thr Gln Asn Val Tyr Lys Ile Pro Pro Thr Thr Thr Lys
            130                 135                 140
Ala Leu Cys Pro Leu Tyr Thr Ser Pro Arg Thr Val Thr Gln Ala Pro
145                 150                 155                 160
Pro Lys Ser Thr Ala Asp Val Ser Thr Pro Asp Ser Glu Ile Asn Leu
                165                 170                 175
Thr Asn Val Thr Asp Ile Ile Arg Val Pro Val Phe Asn Ile Val Ile
                180                 185                 190
Leu Leu Ala Gly Gly Phe Leu Ser Lys Ser Leu Val Phe Ser Val Leu
            195                 200                 205
```

Fig. 16 (B)

Phe Ala Val Thr Leu Arg Ser Phe Val Pro
    210                 215

[SEQ ID NO:10] - Human TREM-1-Receptor (mature protein) amino acid sequence

Fig. 17

```
  1 gagcttgaag gatgaggaag gctgggctct ggggactgct gtgcgtgttc tttgtctcag
 61 aagtcaaagc tgccattgtt ctagaggaag aaaggtatga cctagtggag ggccagactt
121 tgacagtgaa gtgtcccttc aacatcatga agtatgccaa cagccagaag gcttggcaga
181 gactaccaga cgggaaggaa cccttgaccc tggtggtcac acagaggccc tttacaagac
241 ccagtgaagt ccacatgggg aagttcaccc tgaaacatga ccctagtgag gccatgctac
301 aagttcaaat gactgacctt caagtgacag actctggatt gtatcgttgt gtgatttacc
361 atcctccgaa tgaccctgtt gtgctcttcc atcctgtccg cctggtggtg accaagggtt
421 cttcagatgt gttcactcct gtcatcattc ctattacaag gctgacagag cgtcccatcc
481 ttattaccac aaaatactca cccagtgaca caactacaac ccgatcccta cccaagccca
541 ctgcggttgt ttcctctcct ggtcttggag tcactatcat aaatgggaca gatgctgaca
601 gtgtctccac atccagtgtt actatttcag tcatctgtgg acttctcagc aagagcctgg
661 ttttcatcat cttattcatt gtcacaaaga ggacatttgg atgacagaac ttgaagctat
721 acaatagtga ccttcagcgg tgtctatttc acaggaggag ctgaggtggt ggggctgagg
781 aggagctatg acatgaattg aacctgtaat caccggtgac gtctaaggct caggatatcc
841 tcagctgacc ctgtccactc tcctcatttt atccatcatc ttggggatgt gctctgcacc
901 cttagaaaag gggaaaccat tcccagaaca ctctggccat tccccctaaa tagttgggtt
961 ggcctgaaat aaagagaaac tccagagctt
```

[SEQ ID NO:11] - Murine TREM-1-Receptor cDNA sequence (Genbank Accession No. NM_021406)

DIAGNOSTIC AND PROGNOSTIC COMPOUNDS AND METHOD

This invention relates generally to the field of immunology. More particularly, the present invention relates to inflammation and the use of a specific marker as an indication of the activation state of myeloid cells. More specifically, the invention relates to markers that allow the prompt diagnosis of sepsis of infectious (for example bacterial or fungal) origin and the follow up of septic patients during pharmacological treatment.

Sepsis constitutes a significant consumption of intensive care resources and remains an ever-present problem in the intensive care unit. It has been estimated that between 400 000 and 500 000 patients are so affected each year in both the USA and Europe. Morbidity and mortality have remained high despite improvements in both supportive and anti-microbial therapies. Mortality rates vary from 40% for uncomplicated sepsis to 80% in those suffering from septic shock and multi-organ dysfunction. The pathogenesis of the conditions is now becoming better understood. Greater understanding of the complex network of immune, inflammatory and haematological mediators may allow the development of rational and novel therapies.

The condition of sepsis has previously been associated with many terms and nomenclature, reflecting both the complexity of the condition and the similarity of the inflammatory response secondary to other aetiologies. To illustrate the complex nature of sepsis, sepsis has been defined by Edward O. Uthman, MD, as "a constellation of clinical and laboratory findings from which an experienced physician concludes that the patient may have a serious infection". His definition was purposely made as a nebulous, subjective, and tautological definition, because attempts to define "sepsis" in the literature have stirred a great deal of disagreement and qualification.

In 1991, the American College of Chest Physicians and the American Society of Critical Care Medicine published definitions for systemic inflammatory response syndrome (SIRS) and sepsis, with the aim of clarifying the diagnosis and treatment of these conditions and to aid interpretation of research in this field (see Table 1).

A pattern of physiological variables have been shown in critically ill patients in response to a range of insults including; trauma, burns, pancreatitis and infection. These include inflammatory responses, leucocytosis or severe leucopaenia, hyperthermia or hypothermia, tachycardia and tachypnoea and have been collectively termed the systemic inflammatory response syndrome (SIRS). This definition emphasises the importance of the inflammatory process in these conditions regardless of the presence of infection. The term sepsis is reserved for SIRS when infection is suspected or proven.

Sepsis is further stratified into severe sepsis when there is evidence of organ hypoperfusion, made evident by signs of organ dysfunction such as hypoxaemia, oliguria, lactic acidosis or altered cerebral function. Septic shock is severe sepsis complicated by hypotension defined as systolic blood pressure less than 90 mmHg despite adequate fluid resuscitation. Sepsis and SIRS may be complicated by the failure of two or more organs, termed multiple organ failure (MOF), due to disordered organ perfusion and oxygenation. In addition to systemic effects of infection, a systemic inflammatory response may occur in severe inflammatory conditions such as pancreatitis and burns.

The appearance of signs of an inflammatory response is less well defined following traumatic insults. In the intensive care unit, gram-negative bacteria are implicated in 50 to 60% of sepsis cases with gram-positive bacteria accounting for a further 35 to 40% of cases. The remainder of cases are due to the less common causes of fungi, viruses and protozoa.

Early recognition of sepsis and Systemic Inflammatory Response Syndrome (SIRS) in the critically ill patient may avoid the increased morbidity, mortality and length of stay associated with multiple organ failure. However, there are major problems associated with diagnosis of sepsis and a clear need exists for rapid, reliable and sensitive methods to detect, monitor and treat SIRS due to infectious agents (sepsis).

TABLE 1

Definitions for the systemic inflammatory response syndrome (SIRS) and sepsis

| SIRS Two or more of: | 1. Temperature > 38° C. or < 36° C. |
| --- | --- |
| | 2. Tachycardia > 90 beats/minute |
| | 3. Respiratory rate > 20 breaths/minute or $PaCO_2$ < 4.3 kPa |
| | 4. White blood count > $12 \times 10^9$/l or < $4 \times 10^9$/l or > 10% immature (band) forms |
| Sepsis: | SIRS due to infection |
| Severe sepsis: | Sepsis with evidence of organ hypoperfusion |
| Septic shock: | Severe sepsis with hypotension (systolic BP < 90 mmHg) despite adequate fluid resuscitation or the requirement for vasopressors/inotropes to maintain blood pressure |

The present invention is directed towards circumventing the existing problems associated with diagnosing sepsis to provide an accurate and consistent method of detection.

The present invention is based upon the Inventors' surprising finding that the ligand (referred to herein as "TREM-1-Ligand") of a myeloid cell receptor called TREM-1 (referred to herein as "TREM-1-Receptor") is a specific marker for bacterial and fungal sepsis (Systemic Inflammatory Response Syndrome). In other words SIRS caused or exacerbated by bacterial or fungal infection.

Cells of the monocyte/macrophage lineage belong to the innate immune system and lack a highly diverse repertoire of antigen receptors. Nevertheless, their activity is regulated by a variety of activating and inhibitory cell surface receptors. Studies have identified a new family of receptors, the TREM family, whose expression appears restricted to myeloid cells (see Bouchon et al. (2000) *J. Immunol.* 164, 4991-4995). TREM receptors activate myeloid cells via association with the adaptor molecule DAP12.

Recent studies demonstrate that TREM-1-Receptor plays a critical role in the inflammatory response to infection. Expression of TREM-1-Receptor is increased on myeloid cells in response to both bacterial and fungal infections in humans. Similarly, in mice the induction of shock by lipopolysaccharide (LPS) is associated with increased expression of TREM-1-Receptor. Further, treatment of mice with a soluble TREM-1-Receptor/Immunoglobulin fusion protein, as a 'decoy' receptor, protects mice from death due to LPS or *E.coli*. Significant survival benefit upon administration of the soluble receptor has been observed up to four hours after shock induction.

No ligands for TREM-1-Receptor have previously been identified.

As described herein the Inventors have detected TREM-1-Ligand on neutrophils isolated from peripheral neutrophils from patients with bacterial and fungal SIRS. The data described herein demonstrate that: the expression of TREM-1-Ligand has a diagnostic and prognostic value, since its expression is detected exclusively on circulating neutrophils from patients with SIRS of bacterial or fungal origin (sepsis)

and not in SIRS where no infection with extracellular pathogens (eg bacteria and fungi) could be proven. Therefore, its detection permits early recognition of sepsis, allowing earlier intervention In addition, the expression of TREM-1-Ligand on circulating neutrophils from patients with sepsis is completely down-regulated when the patients show clinical signs of recovery. Therefore, the expression of TREM-1-Ligand also allows the monitoring and follow-up of septic patients during the pharmacological treatment of the disease.

Accordingly, the present invention provides methods and compositions for the clinical screening and diagnosis of bacterial or fungal sepsis. In addition, the present invention provides methods and compositions for monitoring the effectiveness of bacterial or fungal sepsis treatment, for selecting participants in clinical trials relating to bacterial or fungal sepsis, for identifying subjects most likely to respond to a particular therapeutic treatment for bacterial or fungal sepsis and for screening and development of drugs for treatment of bacterial or fungal sepsis.

Thus, in a first aspect the invention provides a method of diagnosing bacterial or fungal sepsis in a subject, which method comprises the step of measuring the level of TREM-1-Ligand or TREM-1-Ligand nucleic acid in a biological sample obtained from said subject.

In other words, the invention provides a method of diagnosing or monitoring bacterial or fungal sepsis in a patient, comprising: measuring the level of TREM-1-Ligand or TREM-1-Ligand nucleic acid In a sample from the patient, wherein the level is an indicator of presence or extent of bacterial or fungal sepsis in the patient.

Furthermore, the invention provides a method of diagnosing bacterial or fungal sepsis in a subject which method comprises the step of measuring the binding of a TREM-1 receptor-derived polypeptide to a sample of cells, for example, neutrophils in a biological sample taken from a patient. Alternatively a measurement of the binding of a TREM-1 receptor-derived polypeptide to the components, for example proteins, of a cell-free sample obtained from a biological fluid, can be used to diagnose bacterial or fungal sepsis.

The methods of the invention can comprise the further step of correlating said binding with the presence or absence of bacterial or fungal sepsis. This correlation can be made by comparing the measured level in a biological sample taken from a patient with a mean level in a control sample or reference standard to indicate the presence or extent of bacterial or fungal sepsis in the patient.

The term "bacterial or fungal sepsis" as defined herein, means, SIRS (Systemic Inflammatory Response Syndrome) associated with infection by extracellular pathogens such as bacterial infection, for example bacteremia (the presence of bacteria in the blood) with or without organ failure, and non-bacterial infections, such as fungemia (for example, yeast infection by *Candida albicans*), protozoal infections or parasitemia (such as in filariasis and trypanosomiasis) where increased expression of TREM-1-Ligand can be detected. Without wishing to be bound by theory, the Inventors suspect that TREM-1-Ligand expression is not usually increased in incidences of infection and sepsis caused by intracellular pathogens such as viruses.

"TREM-1-Ligand" as defined herein, is a ligand found on blood cells, in particular circulating neutrophils, in patients with bacterial or fungal sepsis, which is bound by the TREM-1-Receptor. "TREM-1-Ligand nucleic acid" as defined herein is nucleic acid, i.e. mRNA or cDNA which is presumed to be upregulated in patients with bacterial or fungal sepsis to bring about increased levels of "TREM-1-Ligand".

In one embodiment, where the level of TREM-1-Ligand is measured, the measurement of the level of TREM-1-Ligand comprises the steps of (a) contacting said biological sample with a compound capable of binding TREM-1-Ligand; and (b) detecting the level of TREM-1-Ligand present in the sample by observing the level of binding between said compound and TREM-1-Ligand.

The assay or measurement of the sample for the levels of TREM-1-Ligand present in the sample may be carried out using standard protocols known in the art. For example, where the observation of binding between TREM-1-Ligand and the compound capable of binding TREM-1-Ligand takes place, this observation may be carried out using known methodologies. For example the binding may be detected through use of a competitive immunoassay, a non-competitive assay system using techniques such as western blots, a radioimmunoassay, an ELISA (enzyme linked immunosorbent assay), a "sandwich" immunoassay, an immunoprecipitation assay, a precipitin reaction, a gel diffusion precipitin reaction, an immunodiffusion assay, an agglutination assay, a complementfixation assay, an immunoradiometric assay, a fluorescent immunoassay, a protein A immunoassay, an immunoprecipitation assay, an immunohistochemical assay, a competition or sandwich ELISA, a radioimmunoassay, a Western blot assay, an immunohistological assay, an immunocytochemical assay, a dot blot assay, a fluorescence polarization assay, a scintillation proximity assay, a homogeneous time resolved fluorescence assay, a IAsys analysis, and a BIAcore analysis.

For example, where an ELISA assay is performed, a TREM-1-Ligand binding compound is coated to a plate to capture TREM-1-Ligand from a biological sample. A different (e.g. labelled) or the same TREM-1-Ligand binding compound is then used to reveal the presence of TREM-1-Ligand on the plate, for example by it being conjugated to a detectable agent. It will be understood by those skilled in the art that the TREM-1-Ligand binding compound need not be an antibody to be applicable in the immunoassays mentioned above—a soluble form of the TREM-1 receptor, as described herein, can be used in such assays.

In an alternative embodiment, where the level of TREM-1-Ligand nucleic acid is measured, the step of measuring the level of TREM-1-Ligand nucleic acid comprises the steps of (a) contacting said biological sample with an oligonucleotide probe or oligonucleotide primer specific for TREM-1-Ligand nucleic acid and (b) detecting the level of TREM-1-Ligand nucleic acid present in the sample by observing the level of interaction between said oligonucleotide probe or oligonucleotide primer and said TREM-1-Ligand nucleic acid. Such probes and primers predominantly, preferably specifically, bind to TREM-1-Ligand nucleic acid in a manner sufficient to enable detection by known methods. The "level of interaction", for example the level of binding of a probe or the level of amplification brought about by a primer, provides an indication of the level or amount of nucleic acid (for example, cDNA or RNA) present in the sample and thus the level or amount of the TREM-1-Ligand. Such observations may be carried out using known methodologies and protocols. For example, where an oligonucleotide probe is used to detect the level of TREM-1-Ligand nucleic acid, for example mRNA, Northern hybridizations, dot-blot, and in situ hybridizations can be used. Where an oligonucleotide primer is used to detect TREM-1-Ligand nucleic acid, primer extension reactions, such as the polymerase chain reaction (PCR), for example quantitative PCR, can be carried out upon cDNA or RNA samples, to determine the level of TREM-1-Ligand nucleic acid.

The determination of the incidence of sepsis can be undertaken by comparing the levels of TREM-1-Ligand or TREM-1-Ligand nucleic acid present in the sample with those in a control sample, the median level in a group of control samples (for example, samples from healthy individuals) or with data derived from previous analyses (for example provided as a standard curve or illustration with a diagnostic kit of the invention or data within a computer program, for example associated with a diagnostic means of the invention). The determination of the incidence of sepsis may comprise deriving the likelihood ratio using a multivariate analysis based on distribution parameters from a set of reference data derived from analysis of the levels of TREM-1-Ligand or TREM-1-Ligand nucleic acid in patients in which bacterial or fungal sepsis is absent, present or in remission.

The invention therefore also provides diagnostic means capable of measuring levels of TREM-1-Ligand or TREM-1-Ligand nucleic acid and/or comparing said levels to known levels that are indicative of the disease state of sepsis. Such diagnostic means can take the form of a stick test, for example carrying the necessary reagents to perform the method of the invention and to produce, for example, a colorimetric result which can be compared against a colour chart. Other diagnostic means which include a sample measuring means and/or a data processing means containing standard data, as mentioned above, with associated programs for comparing such data with data from a sample are also envisaged.

Thus, in either of the above embodiments, the method according to the first aspect of the invention can comprise the further step of c) correlating the detected level of TREM-1-Ligand or TREM-1-Ligand nucleic acid with the presence or absence of bacterial or fungal sepsis. For example, a correlation can be made by comparing the measured level of TREM-1-Ligand or TREM-1-Ligand nucleic acid in the sample with a mean level in samples obtained from a control population of individuals not having bacterial or fungal sepsis, to indicate the presence or extent of bacterial or fungal sepsis in the patient.

In a further embodiment, the method according to the first aspect of the invention can be used in monitoring the progression or remission of bacterial or fungal sepsis, in other words, to indicate the progression or remission of the bacterial or fungal sepsis. Such methods can be used to monitor the effectiveness and/or progress of bacterial or fungal sepsis therapy in a subject. In this embodiment, the method further comprises the steps of measuring the level of TREM-1-Ligand or TREM-1-Receptor nucleic acid in a second or further sample from the patient, the first and second or further samples being obtained at different times; and comparing the levels in the samples to indicate the progression or remission of the bacterial or fungal sepsis.

The diagnostic methods according to the present invention are carried out ex vivo. Biological samples for analysis by the methods of the invention can be obtained using methods known in the art from various sources, in particular from whole blood, blood serum, blood plasma, urine, cellular fractions of blood and neutrophils isolated from peripheral blood. The sample should be a sample treated such that any TREM-1-Ligand present is not removed prior to the assay or is rendered undetectable.

In addition to cell containing samples, the biological sample can be a cell-free sample, for example a supernatant, obtained from, for example, a biological fluid. In this case, the components, for example proteins, of the sample are immobilised for example on a solid surface, for example by coating onto a plastic surface. The presence of TREM-1-Ligand is then revealed using a TREM-1-Ligand binding compound, which is detected via, for example an antibody or is itself conjugated to a detectable agent.

The methods of the invention are applicable to mammals, for example humans, non-human primates, sheep, pigs, cows, horses, goats, dogs, cats and rodents, such as mouse and rat. Generally, the biological sample tested by the methods of the invention is a human sample. In one embodiment, the biological sample contains protein molecules from the test subject. Alternatively, the biological sample can contain mRNA molecules from the test subject or cDNA molecules from the test subject.

Preferably, the biological sample contains protein molecules from the test subject. A preferred biological sample is a sample of granulocytes isolated from peripheral blood obtained by conventional means from a subject. A particularly preferred sample is a sample containing neutrophils.

In the present application, the term "compound capable of binding TREM-1-Ligand" means polypeptides, ligands, antibodies or otherwise discriminating entities which predominantly, preferably specifically, bind to TREM-1-Ligand. Such binding compounds, or "TREM-1-Ligand binding partners" can be a naturally occurring TREM-1-Ligand binding molecule, for example TREM-1-Receptor and natural and synthetic variants thereof. Further examples of binding compounds include, a chemically modified or genetically modified derivative of a TREM-1-Ligand binding molecule, an artificially (for example chemically produced) TREM-1-Ligand binding molecule or a recombinant or engineered soluble TREM-1-Ligand binding molecule.

Included of use within the scope of the invention are antibodies which bind predominately, preferably specifically or exclusively to, TREM-1-Ligand including, but not limited to, those antibodies which are: mono-or polyclonal antibodies (for example, raised against TREM-1-Ligand), bi-specific, multi-specific, human, humanized, chimeric antibodies, single chain antibodies, antibodies derived from phage display techniques, Fab fragments, F(ab')2 fragments, disulfide-linked Fvs, and fragments containing either a VL or VH domain or even a complementary determining region (CDR) that specifically binds to TREM-1-Ligand. Such antibodies can be obtained according to methods well known in the art. (See, for instance, Chow, M. et al., Proc. Natl. Acad. Sci. USA 82:910-914; and Bittle, F. J. et al., J. Gen. Virol. 66:2347-2354). Immunogenic epitopes of TREM-1-Ligand may be presented together with a carrier protein, such as an albumin, to an animal system (such as rabbit or mouse) or, if long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g. in Western blotting.)

Otherwise modified immunoglobulins are also included within the scope of the invention, for example a fusion of the TREM-1-Receptor to one or more immunoglobulin-derived protein domains, for example to confer solubility and/or stability, for example human IgG or IgM Fc fragments.

In addition, substances or products mimicking the tertiary structure of the TREM-1-Receptor can be used as binding partners specific for TREM-1-Ligand. It is possible to design such on the basis of computer modelling. The product can be produced synthetically using chemical means. Use of recombinant DNA technology to engineer the required structure is also possible as is chemical modification of TREM-1-Receptor-like structures.

Furthermore, it is envisaged that isolated TREM-1-Ligand or computer modelling using the structure of TREM-1-

Ligand, may be used to produce binding partners specific for TREM-1-Ligand using methods known in the art.

In a particular embodiment, a compound capable of binding TREM-1-Ligand can be a modified variant of a naturally occurring TREM-1-Ligand binding molecule, for example the compound capable of binding TREM-1-Ligand can be a polypeptide derived from the TREM-1-Receptor, referred to herein as "a TREM-1-Receptor-derived polypeptide". Suitable "TREM-1-Receptor-derived polypeptides" are discussed further below.

The term "oligonucleotide probe or oligonucleotide primer specific for TREM-1-Ligand nucleic acid" includes any nucleic acid which is capable of binding specifically to TREM-1-Ligand nucleic acid in a manner sufficient to allow detection of TREM-1-Ligand nucleic acid in a hybridization reaction, a primer extension reaction or biochip-based assay as known in the art.

Generally, the oligonucleotide probe or oligonucleotide primer specific for TREM-1-Ligand nucleic acid will interact with TREM-1-Ligand nucleic acid in the sample under the stringent or moderately stringent conditions used in conventional DNA/RNA detection methods. With respect to hybridisation methods such as Northern or Southern analyses, the term "under stringent conditions" refers to hybridization and washing conditions under which nucleotide sequences having at least 60%, preferably 65%, more preferably 70%, most preferably 75% identity to each other remain hybridized to each other. The term "moderately stringent condition" refers to hybridization and washing conditions under which nucleotide sequences having at least 40%, preferably 45%, more preferably 50%, most preferably 55% identity to each other remain hybridized to each other. Such hybridization conditions are described in, for example but not limited to, *Current Protocols in Molecular Biology*, 1989, John Wiley & Sons, New York, 6.3.1-6.3.6., and *Basic Methods in Molecular Biology*, 1986, Elsevier Science Publishing Co., Inc., New York, 1986, pp. 75-78, and 84-87, and are well known to those skilled in the art. A preferred, non-limiting example of stringent hybridization conditions is hybridization in 6× sodium chloride/sodium citrate (SSC) at about 45° C. followed by one or more washes in 0.2×SSC, 0.1% SDS at about 50-65° C. A preferred, non-limiting example of moderately stringent conditions is hybridization in 6×SSC at about 42° C. followed by one or more washes in 0.2×SSC, 0.1% SDS at about 45-55° C.

With respect to primer extension reactions, stringent conditions will depend on the primers used, but will be such that a TREM-1-Ligand nucleic acid template is preferentially amplified to allow detection.

According to a second aspect of the invention there is provided, compounds and pharmaceutical compositions for use in the diagnosis, prognosis, treatment or monitoring of the treatment of bacterial or fungal sepsis.

In one embodiment of this second aspect, the invention provides a compound capable of binding TREM-1-Ligand for use in the diagnosis, prognosis, treatment or monitoring of the treatment of bacterial or fungal sepsis. Also provided are oligonucleotide probes or oligonucleotide primers specific for TREM-1-Ligand for use in the diagnosis, prognosis, treatment or monitoring of the treatment of bacterial or fungal sepsis.

In another embodiment, the invention provides use of a compound capable of binding TREM-1-Ligand or use of oligonucleotide probes or oligonucleotide primers specific for TREM-1-Ligand nucleic acid in a method of diagnosis, prognosis, treatment or monitoring of bacterial or fungal sepsis.

In a further embodiment, the invention provides use of a compound capable of binding TREM-1-Ligand in the manufacture of a medicament for the diagnosis, prognosis, treatment or monitoring of the treatment of bacterial or fungal sepsis.

The methods described herein can furthermore be used as screening assays to identify a subject with, or at risk of developing, bacterial or fungal sepsis. Such assays can be used to determine whether a subject can be administered an agent (e.g., an agonist, antagonist, peptidomimetic, protein, peptide, nucleic acid, small molecule, or other drug candidate) to treat bacterial or fungal sepsis. For example, such methods can be used to determine whether a subject can be effectively treated with a specific agent or class of agents (e.g., antibacterial or antifungal agents). Thus, the present invention provides methods for determining whether a subject can be effectively treated with an agent for bacterial or fungal sepsis in which a test sample is obtained and the TREM-1-Ligand or TREM-1-Ligand nucleic acid is detected A further embodiment of the invention provides a composition (eg a pharmaceutical composition) comprising a compound capable of binding TREM-1-Ligand together with a pharmaceutically acceptable diluent, carrier or excipient for use in the diagnosis or treatment of bacterial or fungal sepsis.

Accordingly, also provided is the use of a compound capable of binding TREM-1-Ligand in a method of treatment or diagnosis of bacterial or fungal sepsis. In other words, the use in diagnosis and treatment of bacterial or fungal sepsis of a compound capable of binding TREM-1-Ligand. The invention also provides a compound capable of binding TREM-1-Ligand for use in, or used in, a method of diagnosis or treatment of bacterial or fungal sepsis.

As used herein the language "pharmaceutically acceptable diluent, carrier or excipient" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be included in a container, pack, or dispenser together with instructions for administration A third aspect of the invention provides a method of identifying modulators of the expression and/or activity of TREM-1-Ligand said method comprising comparing the level of binding in a sample containing said TREM-1-Ligand and a compound capable of binding TREM-1-Ligand, in the presence and absence of a compound to be tested. Also provided by are agonists or antagonists of TREM-1-Ligand identified according to the method of this aspect of the invention. Also provided is a method of screening compounds for use in bacterial or fungal sepsis therapy comprising determining the effect of those compounds on levels of TREM-1-Ligand present in samples brought into contact with said compounds. Accordingly, the invention also provides a method of treating bacterial or fungal sepsis in a subject, which method comprises administering to an individual in need thereof an effective amount of a modulator (eg an inhibitor) of expression or activity of TREM-1-Ligand.

Modulators of expression and/or activity include antagonists (eg inhibitors) and agonists.

In a fourth aspect, the invention provides kits, associated reagents and contacting means. In one embodiment the invention provides a kit comprising at least one compound capable of binding TREM-1-Ligand and reagents for detecting binding of said compound to TREM-1-Ligand.

Another embodiment provides a kit comprising one or more oligonucleotide probes or oligonucleotide primers specific for TREM-1-Ligand nucleic acid and reagents for detecting TREM-1-Ligand nucleic acid by means of said probes or primers.

A further embodiment provides a kit comprising at least one compound capable of binding TREM-1-Ligand or one or more nucleotide probes or primers specific for TREM-1-Ligand nucleic acid and means for contacting said compound or probes or primers with a sample containing said ligand or TREM-1-Ligand nucleic acid.

For TREM-1-Ligand binding compound-based kits, the kit can comprise, for example: (1) a binding compound (e.g., attached to a solid support) that binds to TREM-1-Ligand; and, optionally, (2) a second, different binding compound e.g. an antibody, which binds to either the TREM-1-Ligand or the first binding compound and is conjugated to a detectable agent.

For oligonucleotide-based kits, the kit can comprise, for example: (1) an oligonucleotide, e.g., a detectably labeled oligonucleotide, that hybridizes to a TREM-1-Ligand nucleic acid sequence; or (2) a pair of primers useful for amplifying a TREM-1-Ligand nucleic acid molecule. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container, and all of the various containers are within a single package, along with instructions for determining whether the subject from which the sample is derived is suffering from or is at risk of developing bacterial or fungal sepsis.

As discussed above "TREM-1-Receptor-derived polypeptides" can function as compounds capable of binding TREM-1-Ligand. In a presently preferred embodiment of the invention, a compound capable of binding TREM-1-Ligand is derived from the nucleic acid or amino acid sequence of human TREM-1-Receptor (triggering receptor expressed on myeloid cells) for which the cDNA sequence is given in [SEQ ID NO:1]. The TREM-1-Receptor is expressed on human myeloid cells, is a transmembrane protein of the immunoglobulin superfamily (Ig-SF). The TREM-1-Receptor is a transmembrane glycoprotein having the amino acid sequence of [SEQ ID NO:2] that is selectively expressed on blood neutrophils and a subset of monocytes but not on lymphocytes and other cell types.

Accordingly, the invention encompasses isolated or recombinantly prepared TREM proteins or polypeptides or fragments, homologues, derivatives, or variants thereof, as defined herein, as "TREM-1-Receptor-derived polypeptides" Furthermore, this invention encompasses nucleic acid molecules encoding the "TREM-1-Receptor-derived polypeptides" of the invention, and include cDNA, genomic DNA, and RNA.

In the description of TREM-1-Receptor-derived polypeptides that follows, in accordance with the definition of "compound capable of binding TREM-1-Ligand", the "TREM-1-Receptor-derived polypeptides" thus provided by the invention are those which predominantly, preferably specifically, bind TREM-1-Ligand.

Accordingly, TREM-1-Receptor-derived polypeptides can be encoded by nucleic acid molecules which comprise or consist of a nucleotide sequence that is about 30%, 35%, 40%, 45%, 50%, 55%, 60%, 65%, 70%, 75%, 80%, 85%, 90%, 95%, or 98% identical to the nucleotide sequence of [SEQ ID NO:1], or a complement thereof, or isolated nucleic acid molecules which comprise or consist of about 25, 30, 35, 40, 45, 100, 150, 200, 250, 300, 350, 400, 450, 500, 550, 600, 650, 700, 750, 800, 850, or more contiguous nucleotdes of the nucleotide sequence of [SEQ ID NO:1], or a complement thereof.

TREM-1-Receptor-derived polypeptides can be encoded by a nucleotide sequence encoding a protein having an amino acid sequence that is at least about 40%, 45%, 50%, 55%, 60%, 65%, 70%, 75%, 80%, 85%, 90%, 95%, or 98% identical to the amino acid sequence of [SEQ ID NO:2], or fragments, homologues, derivatives, or variants of said protein, or complement of said nucleic acid molecules.

TREM-1-Receptor-derived polypeptides can be encoded by nucleic acid molecules comprising a nucleotide sequence encoding a protein having an amino acid sequence that comprises or consists of at least about 10, 15, 20, 25, 30, 50, 75, 100, 125, 150, 175, 200, 225, 230 or more contiguous amino acids of [SEQ ID NO:2], or fragments, homologues, derivatives, or variants of said protein, or complements of said nucleic acid molecules.

Furthermore, TREM-1-Receptor-derived polypeptides can be polypeptides or proteins comprising an amino acid sequence that is at least about 40%, 45%, 50%, 55%, 60%, 65%, 70%, 75%, 80%, 85%, 90%, 95%, or 98% identical to the amino acid sequence of [SEQ ID NO:2], or fragments, homologues, derivatives, or variants thereof, or can be polypeptides or proteins comprising an amino acid sequence that comprises or consists of at least about 10, 15, 20, 25, 30, 50, 75, 100, 125, 150, 175, 200, 225, 230 or more contiguous amino acids of [SEQ ID NO:2], or fragments, homologues, derivatives, or variants thereof. In accordance with the statement above, such fragments, homologues, derivatives or variants of TREM-1-Receptor retain the ability or capability to bind TREM-1-Ligand.

The term "homologue," especially "TREM-1-Receptor homologue" as used herein refers to any member of a series of peptides or nucleic acid molecules having the ability or capability to bind TREM-1-Ligand and having sufficient amino acid or nucleotide sequence identity as defined herein. TREM-1-Receptor homologues can be from either the same or different species of animals.

The term "variant" as used herein refers either to a naturally occurring allelic variation of a given peptide or a recombinantly prepared variation of a given peptide or protein in which one or more amino acid residues have been modified by amino acid substitution, addition, or deletion.

The term "derivative" as used herein refers to a variation of a given peptide or protein that is otherwise modified, i.e., by covalent attachment of any type of molecule, preferably having bioactivity, to the peptide or protein, including non-naturally occurring amino acids.

The human TREM-1-Receptor cDNA is 884-nucleotide long (FIG. 11; [SEQ ID NO:1]) and the open reading frame of TREM-1-Receptor is nucleotides 48 to 752 of [SEQ ID NO:1], which encodes a transmembrane protein comprising the 234 amino acid sequence shown in FIG. 12 [SEQ ID NO:2]. As shown in FIG. 12 [SEQ ID NO:2], the deduced amino acid sequence of TREM-1 starts with a hydrophobic signal peptide at amino acid residues 1 to 16 of [SEQ ID NO:2] ([SEQ ID NO:3]) followed by an extracellular region composed of a single Ig-SF domain, encompassing amino acid residues 17 to 200 of [SEQ ID NO:2] ([SEQ ID NO:4]), which contain three potential N-glycosylation sites at amino acid residues 146 to 149 of [SEQ ID NO:2] (Asn-Ser-Thr- Gln; [SEQ ID NO:5]), 190 to 193 of [SEQ ID NO:2] (Asn-Leu-Thr-Asn; [SEQ ID NO:6]), and 193 to 196 of [SEQ ID NO:2] (Asn-Val-Thr-Asp; [SEQ ID NO:7]), and the consensus sequences, Leu-Xaa-Val-Xaa-Cys-Xaa-Tyr (at positions 37-43 of [SEQ ID NO:2]; "Xaa" indicates any amino acid) and Asp-Xaa-Gly-Xaa-Tyr-Xaa-Cys (at positions 107-113 of [SEQ ID NO:2]), characteristic of the intrachain disulfide bridge of the Ig-SF V-type fold. The putative transmembrane domain starts from amino acid residues 201 to 229 of [SEQ ID NO:2] ([SEQ ID NO:8]) and contains a charged lysine residue at position 217. Its cytoplasmic tail consists of 5 amino acid residues ([SEQ ID NO:9]) and appears to contain no signaling motifs.

A "signal sequence" or "signal peptide" as used herein refers to a peptide of at least about 10 to 40 amino acid residues which occurs at the N-terminus of secretory or membrane-bound proteins and contains at least about 50-75% hydrophobic amino acid residues such as alanine, leucine, isoleucine, phenylalanine, proline, tyrosine, tryptophan, or valine. A signal sequence serves to direct a protein containing such a sequence to a lipid bilayer. A signal sequence is usually cleaved during the maturation process of the protein. Thus, the invention also includes the use of the domains and the mature protein resulting from cleavage of such a signal peptide.

Accordingly, a mature TREM comprises one or more of the following domains: (1) an extracellular domain which contains at least one Ig-SF domain; (2) a transmembrane domain; and (3) a cytoplasmic domain.

Thus, in one embodiment, a TREM-1-Receptor-derived polypeptide of use in the invention comprises the amino acid sequence of [SEQ ID NO:2]. In another embodiment, a TREM-1-Receptor-derived polypeptide of the invention is a mature polypeptide which does not contain a signal peptide and comprises amino acid residues 17 to 234 of [SEQ ID NO:2] ([SEQ ID NO:10]). In another aspect, a TREM-1-Receptor-derived polypeptide of the invention comprises the amino acid sequence of [SEQ ID NO:2] except that amino acid residues 1 to 16 of [SEQ ID NO:2] are replaced by a heterologous signal peptide by genetic engineering.

In a particular and preferred embodiment, a TREM-1-Receptor-derived polypeptide of use in the invention comprises an extracellular domain comprising amino acid residues 17 to 200 of [SEQ ID NO:2] ([SEQ ID NO:4]). In another embodiment, a TREM-1-Receptor-derived polypeptide of the invention comprises a transmembrane domain comprising amino acid residues 201 to 229 of [SEQ ID NO:2] ([SEQ ID NO:8]).

Further, a TREM-1-Receptor-derived polypeptide of use in the invention comprises a cytoplasmic domain comprising amino acid residues 230 to 234 of [SEQ ID NO:2] ([SEQ ID NO:9]).

In preferred embodiments, a TREM-1-Receptor-derived polypeptide of use in the invention comprises a fragment of [SEQ ID NO:2] which exhibits binding of TREM-1-Ligand. Such fragments are derived from the extracellular domain comprising amino acid residues 17 to 200 of [SEQ ID NO:2] ([SEQ ID NO:4]).

In addition to the TREM-1-Receptor-derived nucleic acid molecules and polypeptides described above, other polypeptides or nucleic acid molecules suitable for use in the invention are those polypeptides and nucleic acid molecules having the ability to bind (or express a polypeptide which binds) TREM-1-Ligand or TREM-1-Ligand nucleic acid. For example, these can be homologues of TREM-1-Receptor from either the same or different species of animal, preferably from mammals, more preferably from rodents, such as mouse [SEQ ID NO: 11] and rat, and most preferably from human.

Homologues of the TREM-1-Receptor nucleic acid molecule (i.e., [SEQ ID NO:1]) can be isolated based on their close nucleotide sequence identity to the human nucleic acid molecules disclosed herein, by standard hybridization techniques under stringent or moderately stringent conditions, as defined herein below, using the human cDNA or a portion thereof as a hybridization probe.

In another aspect, a variant of a TREM-1-Receptor-derived polypeptide can be used in the methods of the invention in which the amino acid sequences have been modified by genetic engineering in order to either enhance or reduce biological activities of the polypeptides, or change the local structures thereof whilst maintaining or retaining an ability or capability to bind TREM-1-Ligand. Such modifications Include amino acid substitution, deletion, and/or insertion. Amino acid modifications can be made by any method known in the art and various methods are available to and routine for those skilled in the art.

For example, mutagenesis may be performed in accordance with any of the techniques known in the art including, but not limited to, synthesizing an oligonucleotide having one or more modifications within the sequence of a given polypeptide to be modified. Examples of mutagenesis used to obtain sequence variants include site specific mutagenesis, PCR-mediated mutagenesis and treatment with mutagenic agents, such as hydroxylamine.

Preferably, the amino acid residues to be modified are surface exposed residues. Additionally, in making amino acid substitutions, preferably the amino acid residue to be substituted is a conservative amino acid substitution, for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, preferably, the amino acid residue to be modified is not highly or completely conserved across species and/or is critical to maintain the biological activities of the protein.

Accordingly, suitable for use in the invention are nucleic acid molecules encoding a TREM-1-Receptor-derived polypeptide that contains amino acid modifications that are not critical to activity. Thus, an isolated TREM-1-Receptor-derived nucleic acid molecule can be a nucleotide sequence encoding a polypeptide having an amino acid sequence that is at least about 40%, 45%, 50%, 55%, 60%, 65%, 70%, 75%, 80%, 85%, 90%, 95%, or 98% identical to the amino acid sequence of [SEQ ID NO:2 or 4] which has the ability to bind TREM-1-Ligand.

Furthermore, the invention also encompasses derivatives of the TREM-1-Receptor-derived polypeptides of the invention. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids.

TREM-1-Receptor-derived polypeptides can be encoded by and expressed from recombinant expression vectors as known in the art which comprise a nucleic acid encoding a TREM-1-Receptor-derived polypeptide in a form suitable for expression of the nucleic acid in a host cell.

A variety of host-vector systems may be utilized in the present invention to express the protein-coding sequence.

These include but are not limited to bacteria transformed with bacteriophage, DNA, plasmid DNA, or cosmid DNA; microorganisms such as yeast containing yeast vectors; insect cell systems infected with virus (e.g., baculovirus); or mammalian cell systems infected with virus (e.g., vaccinia virus, adenovirus, etc.). The expression elements of vectors vary in their strengths and specificities. Depending on the host-vector system utilized, any one of a number of suitable transcription and translation elements may be used. Alternatively, the recombinant expression vector can be transcribed and translated in vitro, for example using T7 promoter regulatory sequences and T7 polymerase.

In an particular embodiment of the invention, TREM-1-Receptor-derived polypeptides can be a fusion protein comprising a bioactive molecule and one or more domains of TREM-1-Receptor or fragment thereof. In particular, the present invention provides fusion proteins comprising a bioactive molecule (for example, conferring stability, solubility or acting as a reporter moiety or an additional binding moiety) recombinantly fused or chemically conjugated (including both covalent and non-covalent conjugations) to one or more domains of TREM-1-Receptor or fragments thereof.

Thus, the present invention further encompasses fusion proteins in which the TREM-1-Receptor-derived polypeptides of the invention or fragments thereof, are recombinantly fused or chemically conjugated (including both covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences.

In one example, a fusion protein in which a TREM-1-Receptor-derived polypeptide of the invention or a fragment thereof can be fused to sequences derived from various types of immunoglobulins. For example, a TREM-1-Receptor-derived polypeptide of the invention can be fused to a constant region (e.g., hinge, CH2, and CH3 domains) of IgG1 or IgM molecule (human or murine), for example, as described in Examples 1, and 2 herein, so as to make the fused polypeptides or fragments thereof more soluble and stable in vitro and in vivo.

A particular TREM-1-Receptor-derived polypeptide is described in Example 3, in which a fusion protein between the extracellular portion of TREM-1-Receptor and the constant domain of human IgG1 (TREM-1-Receptor-huIgG1) is used to detect levels of TREM-1-Ligand.

In one aspect, the fusion protein comprises a TREM-1-Receptor-derived polypeptide of the invention which is fused to a heterologous signal sequence at its N-terminus. For example, the signal sequence naturally found in the polypeptide of the invention can be replaced by a signal sequence which is derived from a heterologous origin. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et al., supra; and *Current Protocols in Molecular Biology*, 1992, Ausubel, et al., eds., John Wiley & Sons) and the protein A secretory signal (Pharmacia Biotech; Piscataway, N.J.) can be listed. Another example is the gp67 secretory sequence of the baculovirus envelope protein (*Current Protocols in Molecular Biology*, 1992, Ausubel, et al., eds., John Wiley & Sons).

In another embodiment, a TREM-1-Receptor-derived polypeptide of the invention can be fused to tag sequences, e.g., a hexa-histidine peptide, such as the tag provided in a pQE vector (QIAGEN, Inc., 9259 Eton Avenue, Chatsworth, Calif., 91311), or the hemagglutinin "HA" tag, which corresponds to an epitope derived from the influenza hemagglutinin protein (Wilson, et al., 1984, *Cell* 37:767) and the "flag" tag (Knappik, et al, 1994, *Biotechniques* 17(4):754-761). These tags among others, many of which are commercially available, are especially useful for purification of recombinantly produced TREM-1-Receptor-derived polypeptides.

Fusion proteins can be produced by standard recombinant DNA techniques or by protein synthetic techniques, e.g., by use of a peptide synthesizer. Once a fusion protein of the invention has been produced by recombinant expression, it may be purified by any method known in the art for purification of a protein, for example, by chromatography (e.g., ion exchange, affinity, particularly by affinity for the specific antibody, and sizing column chromatography), centrifugation, differential solubility, or by any other standard technique for the purification of proteins.

Aspects of the invention can be also applied in the framework of multiple diagnosis of a subject. For example, in a method of screening a patient for presence or susceptibility to disease, comprising performing a plurality of diagnostic tests on a tissue sample from the patient for a plurality of diseases, the invention provides the improvement wherein one of the diagnostic tests comprises measuring the level of TREM-1-Ligand or TREM-1-Ligand nucleic acid.

The various aspects and embodiments of the invention described above also apply to the following: a diagnostic means for detecting bacterial or fungal sepsis; a diagnostic kit comprising such a diagnostic means; a method of treatment of infection, which includes the step of screening an individual for bacterial or fungal sepsis, wherein sepsis is correlated with the levels of TREM-1-Ligand or TREM-1-Ligand nucleic acid in a sample from said individual, and if sepsis is identified, treating that individual to prevent or reduce the infection; and the use, in the manufacture of means for detecting sepsis, of a compound capable of binding TREM-1-Ligand.

All publications, including but not limited to patents and patent applications, cited in this specification are herein incorporated by reference as if each individual publication were specifically and individually indicated to be incorporated by reference herein as though fully set forth.

Preferred features of each aspect of the invention are applicable to each other aspect, mutatis mutandis.

BRIEF DESCRIPTION OF THE DRAWINGS

The present invention will now be described with reference to the following non-limiting examples, with reference to the figures, in which:

FIG. 11. shows Human TREM-1-Receptor cDNA [SEQ ID NO:1].

FIG. 12. FIGS. 12A and 12B show Human TREM-1-Receptor amino acid sequences [SEQ ID NO: 2].

FIG. 13. shows Human TREM-1-Receptor (signal peptide) amino acid sequence [SEQ ID NO:3].

FIG. 14. shows Human TREM-1-Receptor (extra-cellular region) amino acid sequence [SEQ ID NO:4].

FIG. 15. shows Human TREM-1-Receptor (N-glycosylation site) amino acid sequence [SEQ ID NO:5], Human TREM-1-Receptor (N-glycosylation site) amino acid sequences [SEQ ID NO:6, 7 and 8], and Human TREM-1-Receptor (cytoplasmic tail) amino acid sequence [SEQ ID NO:9].

FIG. 16. FIGS. 16A and 16B show Human TREM-1 Receptor (mature protein) amino acid sequence [SEQ ID NO: 10].

FIG. 17. shows Murine TREM-1-Receptor cDNA sequence [SEQ ID NO:11] (Genbank Accession No. NM_021406)

cDNA is synthesized and amplified using SMART™ PCR Synthesis kit (*BD Bioscience Clontech*) following the manufacturer's instructions. Amplified cDNA is then prepared for subtraction using both the SMART™ PCR cDNA Synthesis kit and the PCR-Select™ cDNA Subtraction kit following the manufacturer's instruction. Briefly, cDNA is digested with RsaI and purified. Different adaptors are ligated to the ends of separated populations of target cDNA. Lane 1=Mw markers; lane 2=tester, lane 3=subtracted; lane 4=driver.

Figure 20:
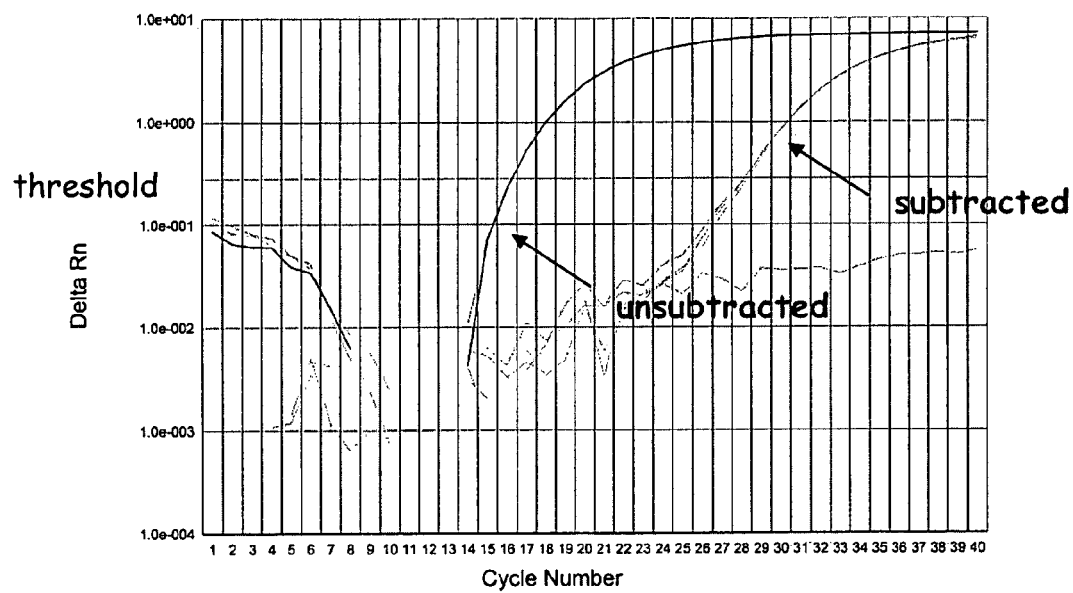

FIG. 20. shows real time PCR of mouse beta-actin in both subtracted and un-subtracted populations.

Figure 21:
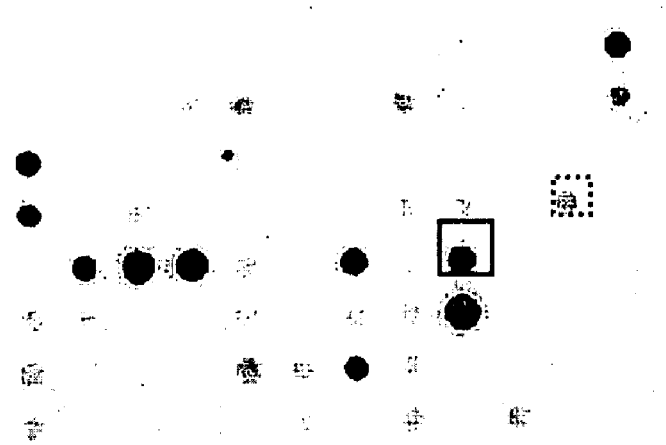
Figure 22:
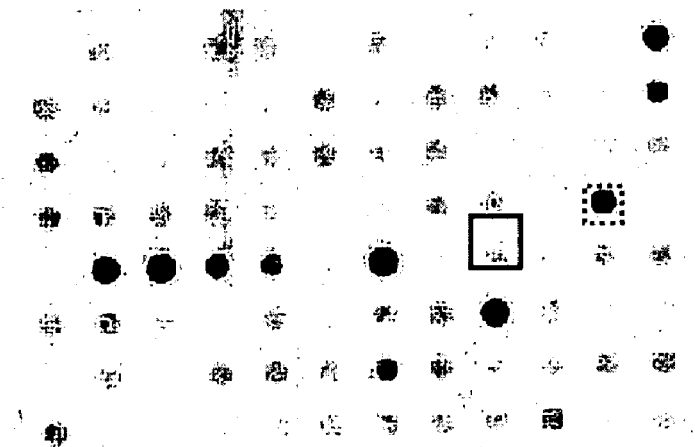

FIGS. 21 (TREM-1-Ligand positive) and 22 (TREM-1-Ligand negative). show the screening of a library performed using $^{32}$P probes from un-subtracted or subtracted cDNA as described in Example 4. Solid squares=genes expressed in CLP mice but not in normal mice; dotted squares=genes expressed in normal mice but not in CLP mice.

EXAMPLES

Example 1

TREM-1-Ligand is Expressed on Neutrophils of Septic Mice

Methods

Production of murine TREM-1-Receptor/human IgG fusion protein To produce murine TREM-1-Receptor (mTREM-1-Receptor) [SEQ ID NO:11] as a soluble fusion protein, a chimeric gene consisting of the mTREM-1-Receptor extracellular domain (GenBank accession number NM_021406) and human IgG constant regions was constructed using the plasmid pCD4 (Traunecker et al., 1991, *Trends Biotechnol.*, 9:109) which is derived from plasmid pHT4-Y1 which can be prepared as previously described by Traunecker, Lüke and Karjalainen in Nature 331, 84-86 (1988) and EP0394827. The cDNA fragment encoding the mTREM-1-Receptor extracellular region was amplified by PCR from cloned plasmid DNA. The forward primer (TAG-TAGAAGCTTATACTTACCGTCAGCATCT-GTCCCATTTAT) [SEQ ID NO: 12] contained a HindIII restriction site and the TREM-1 start codon. The reverse primer (TAGTAGGAATTCAGGATGAGGMGGCTGGG) [SEQ ID NO: 13] provided an EcoR1 restriction site. The ~640-bp PCR product was cut with HindIII and EcoRI, and ligated into an expression vector containing the exons for hinge, CH2 and CH3 regions of human IgG, the guanosine phosphotransferase gene conferring resistance to mycophenolic acid, and the k promoter for the expression in the mouse myeloma cell line J558L. Transfection, screening of culture supernatants and purification of mTREM-1-Receptor-IgG were performed as described (Bouchon et al., Nature 410: 1103, 2001).

Quantification of mTREM-1-Receptor/IgG Fusion Protein.

Purified murine IgG fusion proteins were assayed for specificity, titer and functionality by ELISA using anti human IgG as a capturing protein and specific biotinylated mAb against mTREM-1-Receptor (50D1, rat IgG1,κ) followed by streptavidin-HRP. Immunoblot analysis of purified human IgG fusion proteins revealed only one band of immunoreactivity.

Cecal Ligation and Puncture (CLP).

CLP was performed as described previously (FIG. 1). Briefly, C57BU6 mice were anaesthetised by intraperitoneal administration of 75 mg/kg Ketanest® (Parke Davies & Company, Munich, Germany) and 16 mg/kg Rompun® (Bayer A G, Leverkusen, Germany) in 0.2 ml sterile pyrogen-free saline (B. Braun Melsungen AG, Melsungen, Germany). The caecum was exposed through a 1.0-1.5 cm abdominal midline incision and subjected to a 50-80% ligation of the distal half followed by a single puncture with a G23 needle. A small amount of stool was expelled from the punctures to ensure patency. Then the caecum was replaced into the peritoneal cavity and the abdominal incision closed in layers with 5/0 Prolene thread (Ethicon, Norderstedt, Germany). 500 μl sterile saline containing 1 mg of mTREM-1-Receptor-IgG1 or 1 mg huIgG1,κ (Sigma) was injected intraperitoneally immediately after CLP. The CLP was performed blinded to the identity of the treatment group. Survival after CLP was assessed 4-6 times a day for at least 7 days.

Analysis of Blood and Peritoneal Lavage Fluids

Blood (250 μl) was collected from the tail vein of mice into a Serum Separator Tube (Becton Dickinson) at different time points after induction of CLP. Peritoneal lavage cells were harvested at different time points after CLP induction. Total cell numbers were determined on a Coulter counter and differential counts were performed according to standard morphological criteria on cytospin preparations stained with Giemsa & May-Gruenwald solution (Sigma). A minimum of 200 cells were counted per field, with 3 fields per sample for peritoneal lavage.

Visualization of Murine TREM-1-Ligand in Normal and Septic Mice.

For whole blood staining, 150 μl of 1:2-diluted blood from both normal mice (right plots) and septic mice (left plots) were incubated with FcγIII/II block Mab for 20 min RT. Blood cells were further stained with 8 μg/sample of mTREM-1-Receptor/IgG (top plots) and huIgG (bottom plots) fluorescent tetramers. Briefly, 32 μg of murine TREM-1-Receptor-IgG or human IgG as a control, were complexed with Protein A Alexa 488-conjugated (Molecular Probes) at 4:1 molar ratio for 30 min at RT in PBS/BSA 0.5% buffer, in the dark. Multimer staining were carried out in 150 μl PBS/BSA buffer for 1 hr on ice, in the presence of further 2 μg huIgG per sample, in order to completely block non specific binding sites of protein A. Samples were washed twice with PBS/BSA and further stained with anti Ly-6G-PE antibody. Red blood cells were eventually lysed by using BD lysing solution, before analysing the samples by cytofluorimetric analysis. Cells recovered from peritoneal cavity of either normal or CLP-treated mice were blocked with anti-FcγIII/II MAb (10 μg/ml) (Pharmingen) for 20 min at room temperature. Cells were further stained with mTREM-1-Receptor/IgG or huTREM-1-Receptor/IgM supernatants (fusion protein concentration >40 μg/ml), 1 ml/sample, 20 min on ice. After wash, samples were incubated with anti human IgG-PE and anti Ly-6G-FITC antibody under standard staining conditions, and then subjected to cytofluorimetric analysis.

Results

Figure 1:
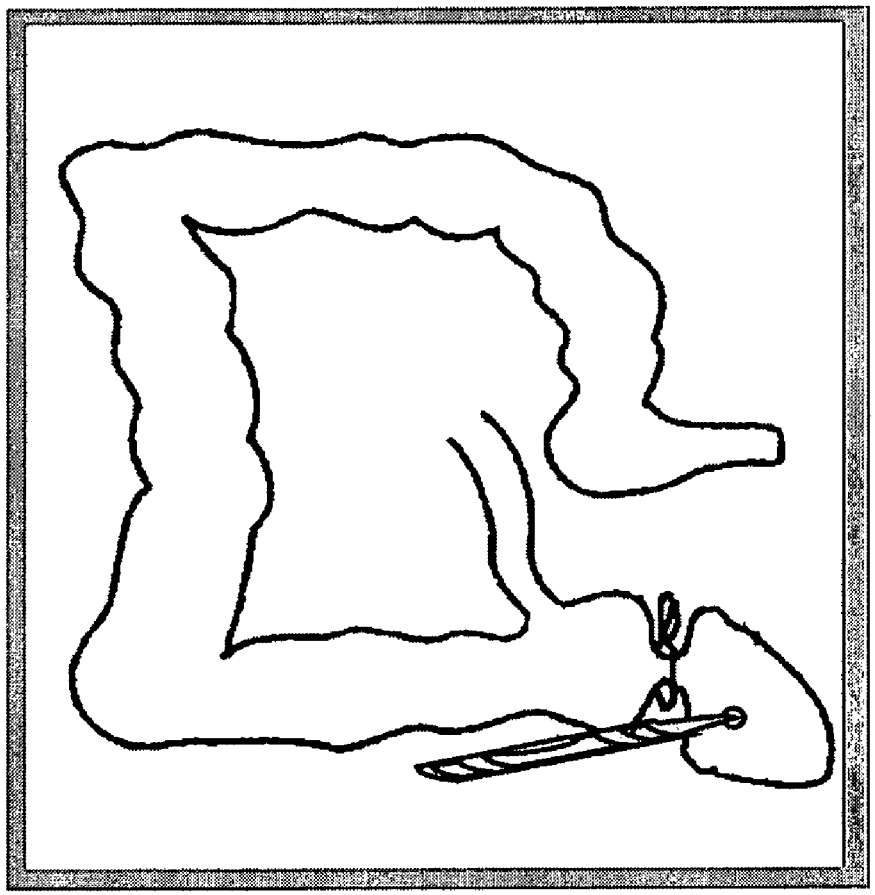
FIG. 1. shows a scheme of the cecal ligation and puncture (CLP) mouse model of sepsis. C57BLU6 mice were anaesthetised and the caecum was exposed through an abdominal midline incision and subjected to a 50-80% ligation of the distal half followed by a single puncture with a G23 needle. A small amount of stool was expelled from the punctures to ensure patency. Then the caecum was replaced into the peritoneal cavity and the abdominal incision closed in layers. Survival after CLP was assessed 4-6 times a day for at least 7 days.
Figure 2:
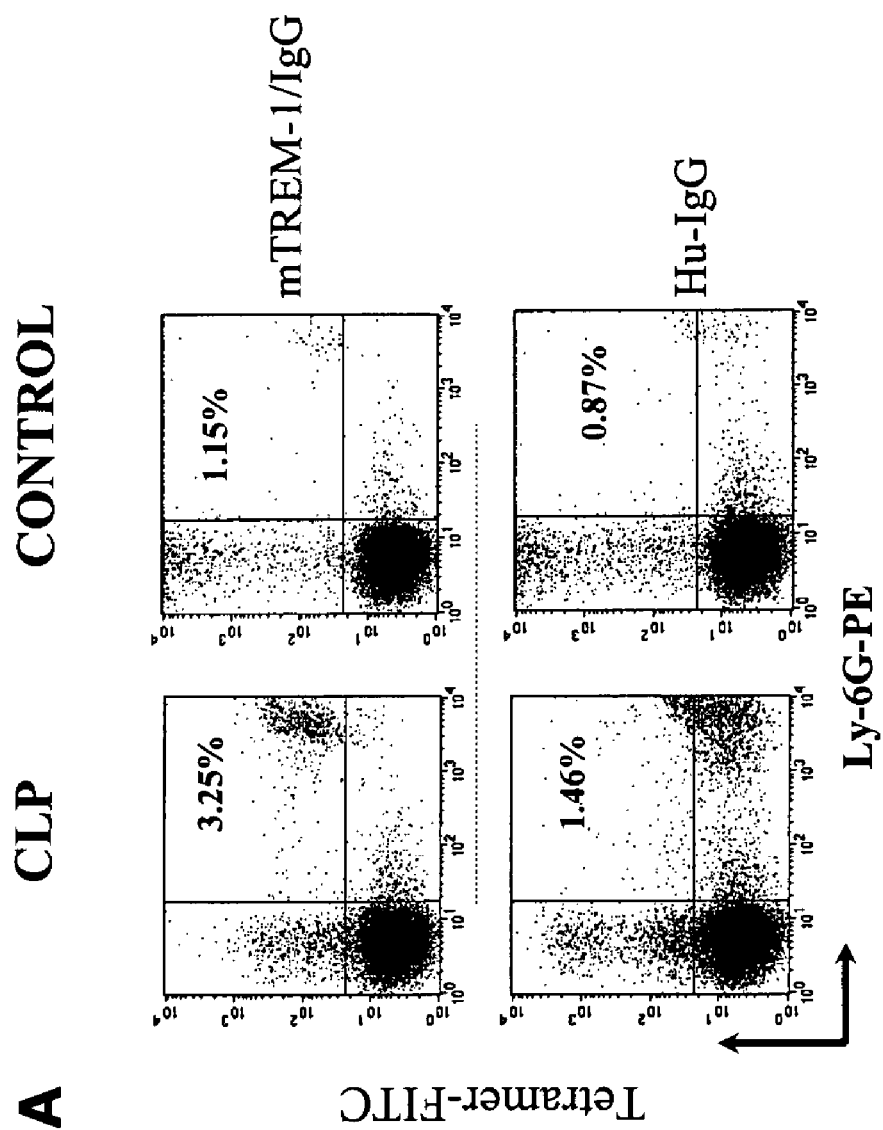
FIG. 2. shows a visualization of murine TREM-1-Ligand in normal and septic mice. Panel A) Whole blood staining. Cells in whole blood were double stained with murine TREM-1-Receptor/IgG fluorescent tetramer and Ly-6G (top plots) or human IgG fluorescent tetramer and Ly-6G (bottom plots). The frequencies of the double positive population in one representative control mouse and one septic (CLP) mouse are indicated. Panel B) Peritoneal cell staining. Cells in the peritoneal cavity of either normal or septic (CLP) mice were stained with murine TREM-1-Receptor/IgG or human TREM-1-Receptor/IgM. The overall frequency of Ly-6G positive, murine TREM-1-Receptor/IgG positive cells in a representative control mouse is 8.8% compared to 35% that were detected in peritoneal cells derived from a representative septic (CLP) mouse. Histogram plots show the frequency of double positive populations in the low Ly-6G (40% in the control mouse and 77% in the septic mouse) and high Ly-6G (33% in the septic mouse) expressing cell subsets.
Figure 3:
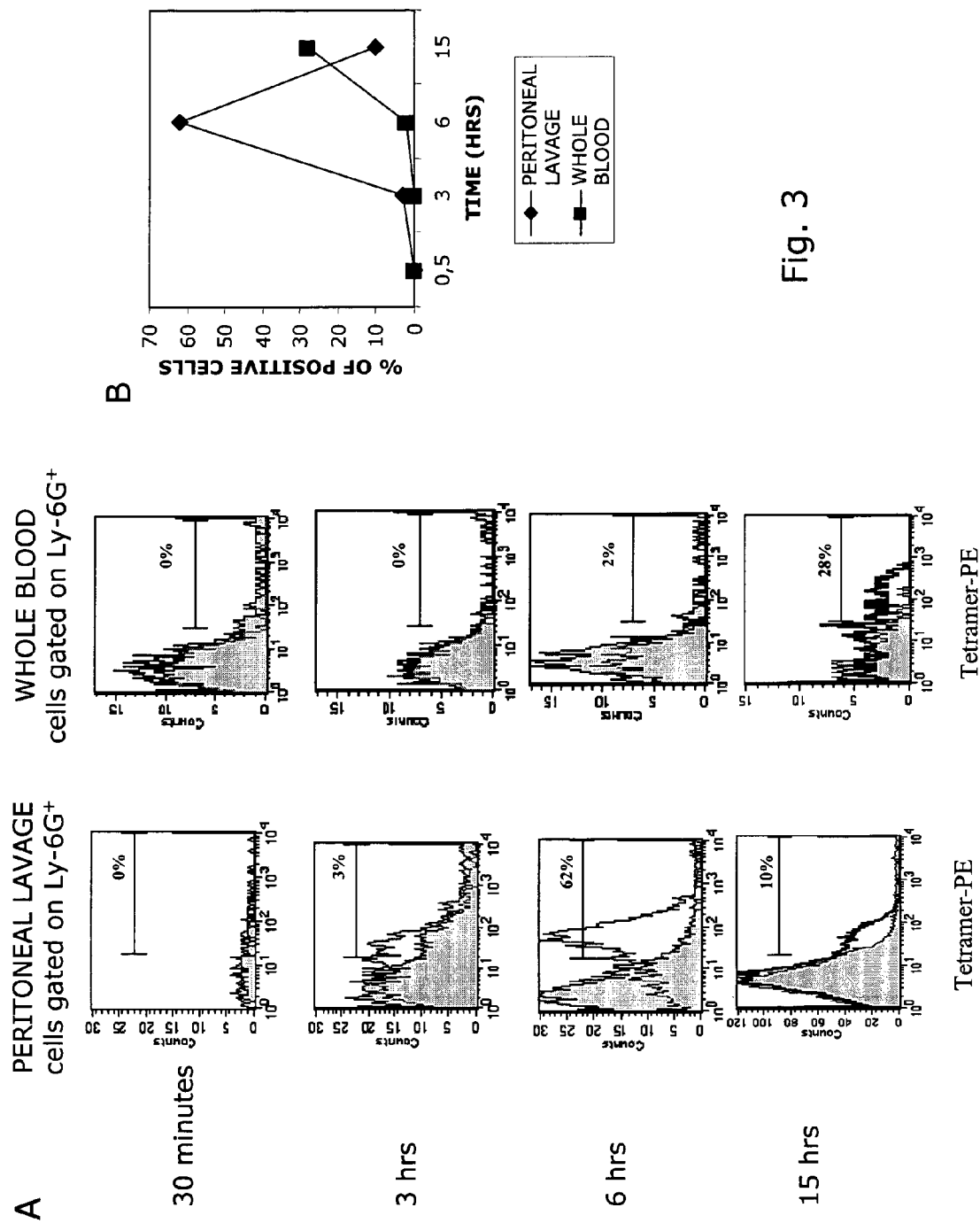
FIG. 3. shows a time course of the expression of TREM-1-Ligand on peritoneal granulocytes of septic mice. Cells were recovered from peritoneal lavage and whole blood of septic (CLP) mice at different times (30 min, 3 hrs, 6 hrs) after CLP induction and then stained with Ly-6G-PE and mTREM-1-Receptor/IgG-tetramer-Alexa 488. Panel A shows histogram plots showing the percentages of mTREM-1-Receptor-IgG-tetramer positive cells within the gated Ly-6G positive cell population in septic mice. Panel B shows a time course of TREM-1-Ligand expression in peritoneal lavage and whole blood of septic mice.

The ligand for murine TREM-1 is up-regulated under septic conditions, in the cecal ligation and puncture model (CLP) (FIG. 1). By using two different staining approaches, a mTREM-1-Receptor/IgG tetramer (panel A) and monomer (panel B), we detected cells that specifically bind the mTREM-1-Receptor fusion protein, indicating the presence of ligand on the cell surface (FIG. 2). Staining is particularly evident in neutrophils obtained from the peritoneal cavity of septic mice. Few TREM-1-Ligand positive appear to be present also in normal, non-septic conditions, but at a much lower extent compared to septic mice. Human TREM-1 fusion protein does not stain murine cells and it is used as a negative control under the same staining conditions. As shown in FIG. 3, TREM-1-Ligand expression appears to be upregulated in peritoneal cells from septic mice between 3 and 6 hours after CLP induction. The kinetics of TREM-1-Ligand expression in cells isolated from the blood of septic mice is slower since 6 hours after CLP induction, only 2% of Ly-6G positive cells express TREM-1-Ligand. However, TREM-1-Ligand is well detected in cells isolated from the blood of septic mice 15 hours after CLP induction.

Example 2

TREM-1-Ligand is Expressed on Circulating Neutrophils of Patients with Septic Shock Methods Production of Human TREM-1-Receptor/Human IgM Fusion Protein To produce human TREM-1-Receptor (huTREM-1) as a soluble fusion protein, the cDNA fragment encoding the huTREM-1 (GenBank accession number AF1 96329) extracellular region [SEQ ID NO: 6] was amplified by PCR with forward primer (TAGTAGGAGCTCACAGGAAGGAT-GAGGAAGACCAGGCTC) [SEQ ID NO: 14] containing an SstI restriction site and blunt reverse primer (AAGCT-TATACTTACCCCTGATGATATCTGTCACATTTGT) [SEQ ID NO: 15] and cloned into an expression vector containing the exons for hinge, CH2, and CH3 region of human IgM. This vector is a derivative of plasmid pCD4 (Traunecker et al., 1991, *Trends Biotechnol.*, 9:109) which is derived from plasmid pHT4-Y1 which can be prepared as previously described by Traunecker, Loke and Karjalainen in Nature 331, 84-86 (1988) and EP0394827. Transfection of the chimeric gene into the mouse myeloma cell line J558L, screening of culture supernatants, and purification of huTREM-1/IgM were performed as previously described (Traunecker et al., 1991, *Trends Biotechnol.*, 9:109).

Quantification of Human TREM-1/Human IgM Fusion Proteins

Purified human IgM fusion proteins were assayed for specificity, titer and functionality by ELISA using anti-human IgG/IgM (Jackson Laboratories) as a capturing protein and a specific biotinylated mAb against huTREM-1-Receptor (21C7, murine IgG1,κ), followed by streptavidin-HRP. Immunoblot analysis of purified human IgM fusion proteins revealed only one band of immunoreactivity.

Isolation of Peripheral Blood Neutrophils.

Peripheral blood from 26 patients with Systemic Inflammatory Response Syndrome (SIRS) were analyzed: 12 patients with associated systemic bacterial/fungal infections (sepsis) and 14 with SIRS from different clinical insults without any evidence of systemic bacterial and fungal infection. Peripheral blood was collected soon after diagnosis of SIRS and sepsis, before initiation of any antibiotic and steroid treatment. All patients had body temperature>38° C., heart rate >90/min, and white cell count >12×10$^9$/l. A second peripheral blood sample was obtained after recovery, defined as normalization of the above clinical parameters. Expression of TREM-1-Ligand was evaluated at the above described time-points.

Staining of Peripheral Blood Neutrophils.

Peripheral granulocytes were isolated from blood by dextran sulfate and subsequent Ficoll gradient. Purified cells were then stained with anti TREM-1 Mab and huTREM-1/IgM. Briefly, cells were pre-incubated with human IgG (Sigma) to block free Fc binding sites. Supernatant (100 μl=1 μg) of soluble TREM-1/IgM was added and incubated 30 minutes at 4° C. After washing, 1 μl of F(ab)$_2$ donkey anti-human IgG1-PE (Jackson Immunoresearch) were added. After washing, cells were resuspended and analyzed by flow cytometry (FACS LSR, Becton Dickinson). Negative control was performed staining granulocytes with purified human IgM. In some cases, double staining with anti CD15 (Pharmingen) was performed.

Statistical Analysis

Statistical analysis was performed by Kruskal-Wallis test.

Results

Figure 4:
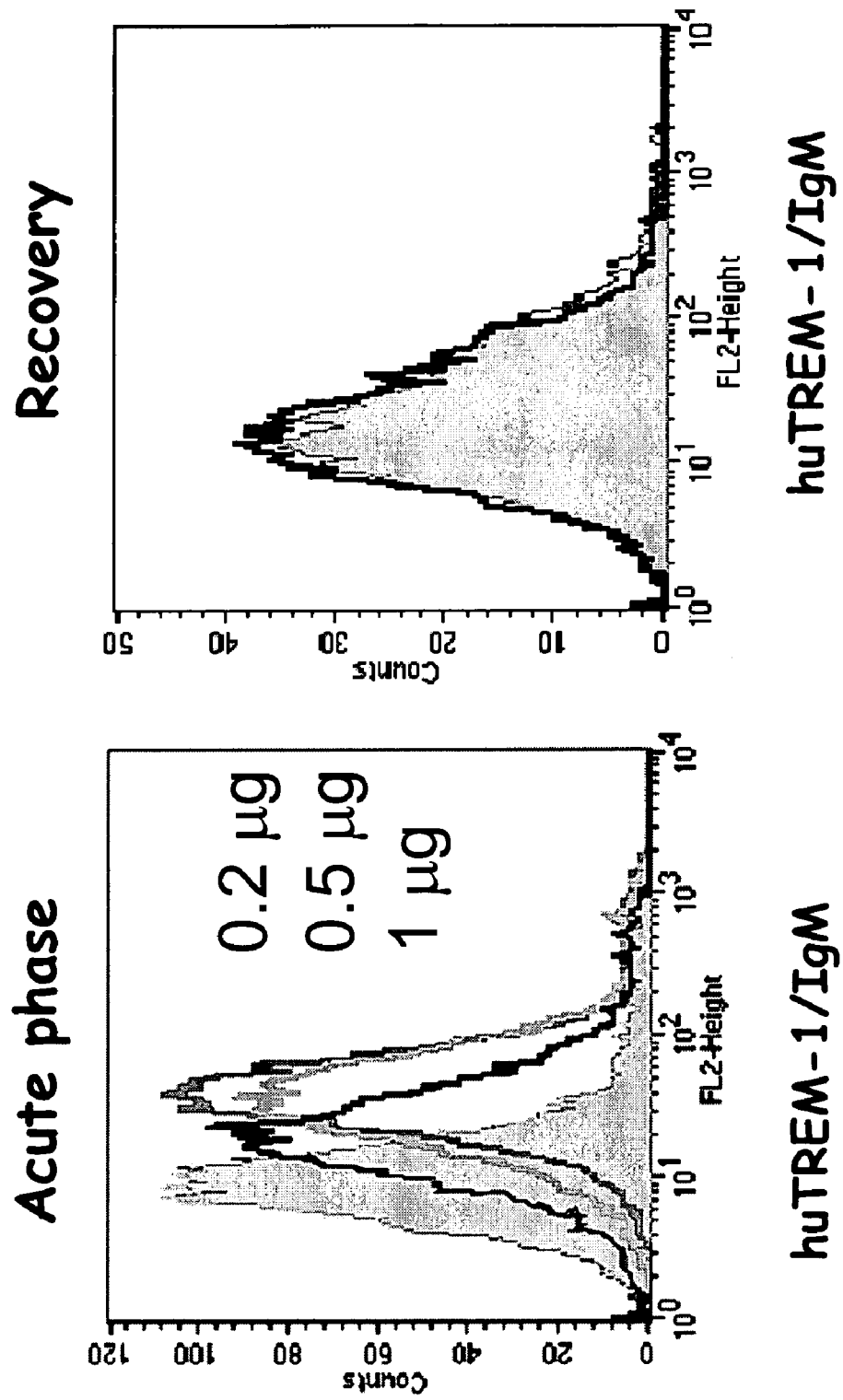
FIG. 4. shows that TREM-1-Ligand is expressed on peripheral neutrophils from patients with sepsis: dose-dependent staining with soluble huTREM-1/IgM. Neutrophils isolated from peripheral blood of patients with sepsis were stained with different concentrations of huTREM-1/IgM: 0.2, 0.5, 1 µg/ml. Histogram plots represent expression of TREM-1-Ligand in one representative patient with sepsis in the acute phase and at the time of recovery.
Figure 5:
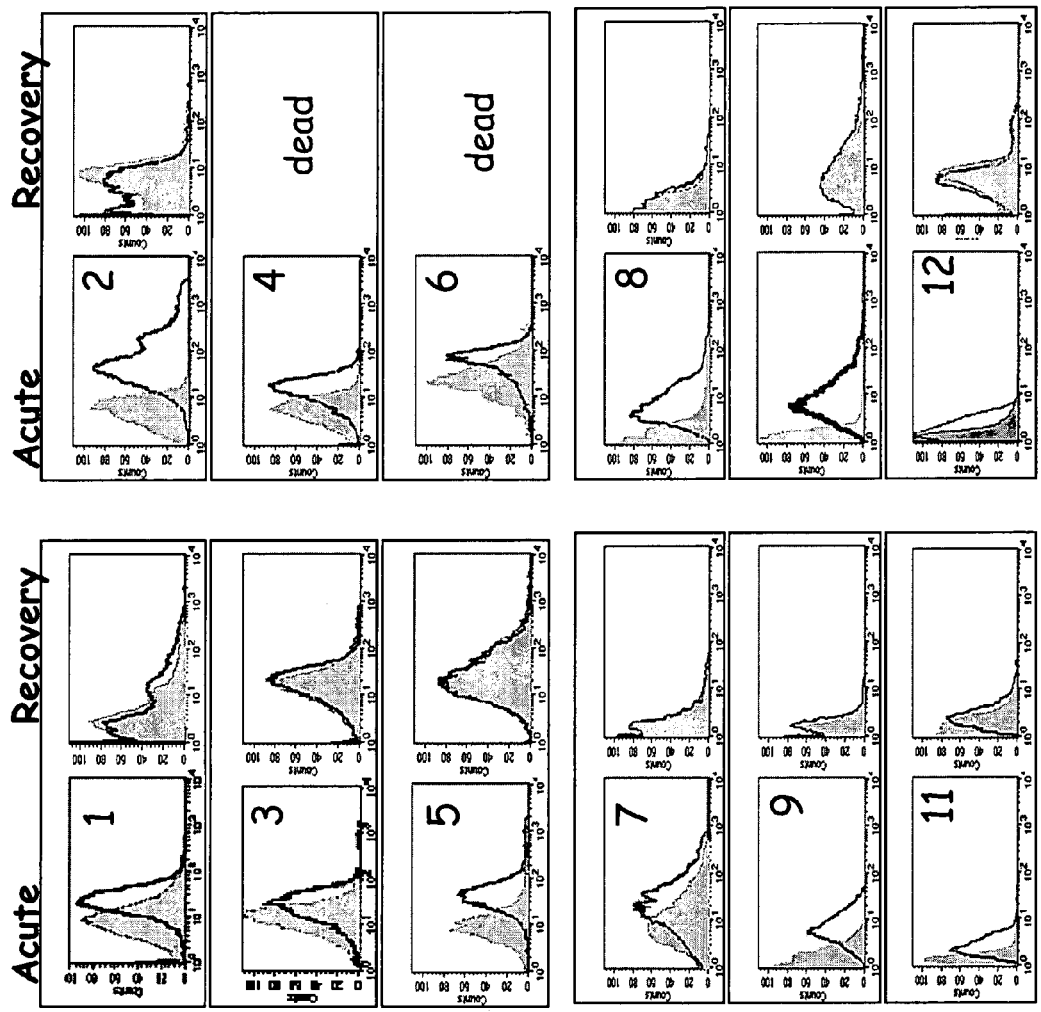
FIG. 5. shows expression of TREM-1-Ligand on peripheral neutrophils of patients with sepsis. Histograms plots represent expression of TREM-1-Ligand in the 12 individual patients with sepsis included in the study. Neutrophils isolated from peripheral blood as described herein, were stained with huTREM-1/IgM and analyzed by flow cytometry (empty histograms) at the time of acute disease and after recovery. The second time point is missing in two patients whose blood samples were not made available because the patients died of septic shock. Filled histograms represent staining with control IgM.

Peripheral blood neutrophils obtained from 14 patients with SIRS (Systemic Inflammatory Response Syndrome) and 12 patients with sepsis were analyzed for expression of TREM-1 and TREM-1-Ligand. Patients were classified based on the criteria indicated in FIG. 4. TREM-1 is constitutively expressed on peripheral neutrophils and its expression is only minimally regulated during SIRS or sepsis. Peripheral neutrophils from patients with SIRS and sepsis were incubated with soluble huTREM-1/IgM fusion protein in order to detect surface expression of TREM-1-Ligand. The staining with huTREM-1/IgM was specific and dose dependent. As shown in FIG. 4, the number of positive cells was proportional to the amount of huTREM-1/IgM used for the staining. With 1 μg huTREM-1/IgM, 80% of the cells stained positive, while with 0.2 μg, only 45% of the cells stained positive. A high percentage of peripheral neutrophils isolated from patients with sepsis stained positive with human TREM-1/IgM, indicating that they expressed TREM-1-Ligand on the cell surface (FIG. 5). However, when peripheral neutrophils from the same patients were analyzed at the time of recovery, the percentage of the cells expressing TREM-1-Ligand was dramatically reduced. This pattern of TREM-1-Ligand expression was observed in all of the 12 patients with sepsis that were analyzed in the study, independently of the bacterial strain that was isolated from their blood culture (Table 2).

TABLE 2

Bacterial strains isolated from blood culture of patients with sepsis. A total of 12 patients with sepsis were analyzed in the study. All of them had an identifiable bacterial strain isolated from their blood cultures. In one case *Candida albicans* was isolated from the blood culture.

| PATIENT | ETHIOLOGY |
| --- | --- |
| 1 | *Pseudomonas aeruginosa* |
| 2 | *Staphilococcus aureus* |
| 3 | *Pseudomonas aeruginosa* |
| 4 | *Candida albicans* |
| 5 | *Serratia marcescens* |
| 6 | *Staphilococcus aureus* |
| 7 | *Staphilococcus aureus* |
| 8 | *Escherichia coli* |
| 9 | *Neisseria meningitidis* |
| 10 | *Haemophilus influenzae* |
| 11 | *Streptococcus pyogenes* |
| 12 | *Staphilococcus aureus* |

Figure 6:
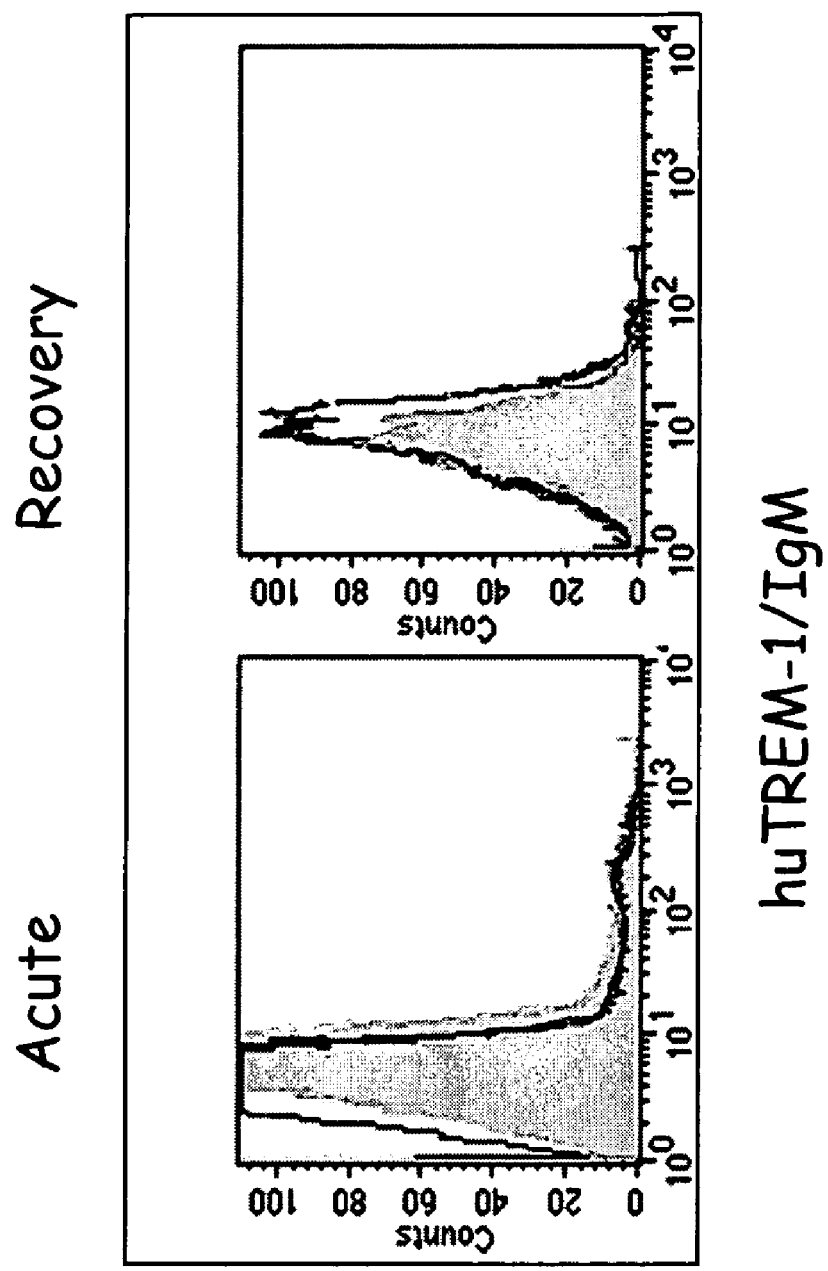
FIG. 6. shows expression of TREM-1-Ligand in a representative patient with Systemic Inflammatory Response Syndrome (SIRS) not associated with sepsis (central hyperthermia). Peripheral blood neutrophils were analyzed as described in the legend to FIG. 5.

These data indicate that down-regulation of the expression of TREM-1-Ligand associated with positive outcome of the disease. Interestingly, TREM-1-Ligand expression was not detected on peripheral neutrophils from patients with SIRS resulting from a range of insults, including trauma, meningitis, pneumonia (Table 3 and FIG. 6). Therefore, TREM-1-Ligand expression was a specific marker of sepsis.

TABLE 3

Clinical diagnosis of patients with Systemic Inflammatory Response Syndrome (SIRS) not associated with sepsis. A total of 14 patients with SIRS were analyzed in the study. The patients were admitted to the Intensive Care Unit with different diagnoses that are listed here. No bacteria/fungi were isolated from their blood.

| DIAGNOSIS | NUMBER OF PATIENTS |
|---|---|
| Neurological coma | 2 |
| Central hypertermia | 3 |
| Meningitis | 1 |
| Multiple Organ Failure | 2 |
| Trauma | 2 |
| Pneumonia | 2 |
| Not diagnosed | 2 |

Figure 7:
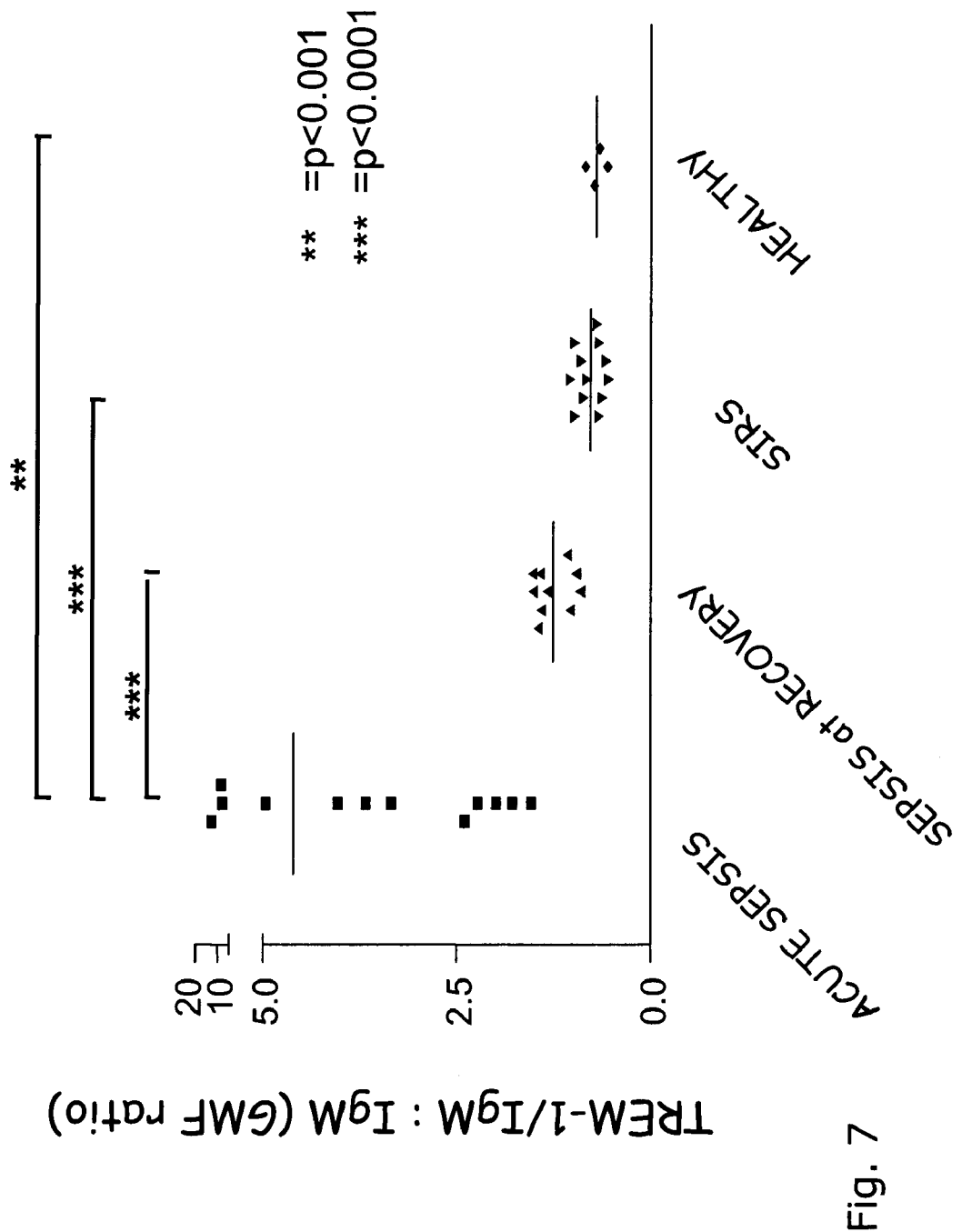
FIG. 7. shows TREM-1-Ligand expression on peripheral blood neutrophils of patients with sepsis and SIRS of non-infectious origin. Individual data of TREM-1-Ligand expression are reported. Data are reported as ratio between the geometric mean fluorescence of cells stained with huTREM-1-Receptor/IgM and the geometric mean fluorescence of cells stained with control IgM. A statistically significant difference was observed between the sepsis in the acute phase and sepsis at recovery ($p<0.0001$) and between sepsis and SIRS ($p<0.0001$). The sepsis group also differs significantly from the healthy control group ($p<0.001$). Statistical analysis was performed with Kruskal-Wallis test.

The expression of TREM-1-Ligand in patients with sepsis in the acute phase and after recovery, and in patients with SIRS is summarized in FIG. 7, where individual data of expression are reported. Data are reported as ratio between the geometric mean fluorescence of cells stained with huTREM-1/IgM and geometric mean fluorescence of cells stained with control IgM. A statistically significant difference was observed between the sepsis in the acute phase and sepsis at recovery ($p<0.0001$) and between sepsis and SIRS ($p<0.0001$). The sepsis group also differs significantly from the healthy control group ($p<0.001$).

Figure 8:
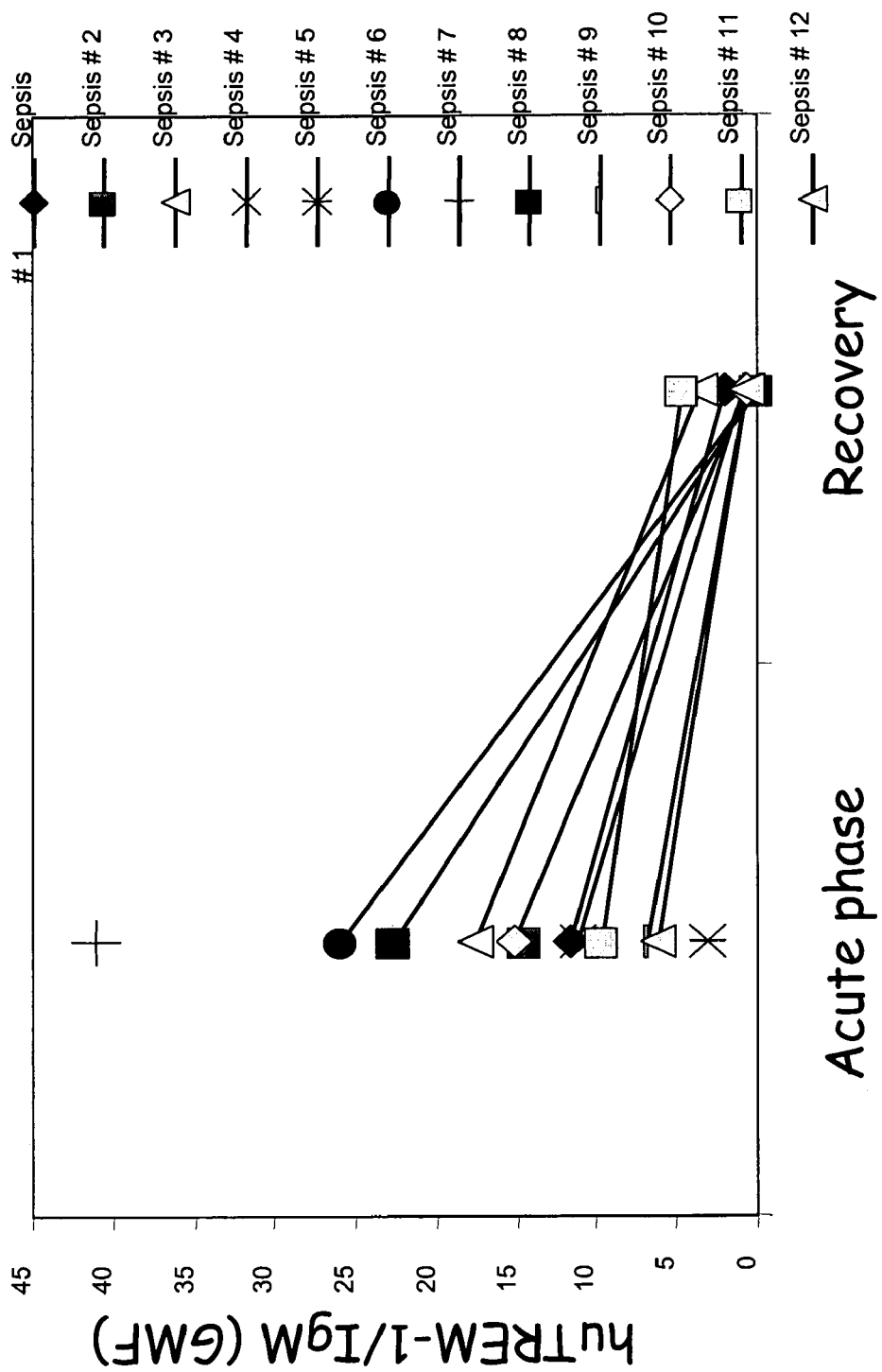
FIG. 8. shows a time course of TREM-1-Ligand expression on peripheral blood neutrophils of patients with sepsis. The Geometric Mean Fluorescence (GMF) of TREM-1-Ligand in sepsis patients in the acute phase and at the time of recovery is reported. Down-regulation of TREM-1-Ligand is observed in all septic patients analyzed, except in those two cases where a second sample was not made available because the patients died.

A time course of the expression of TREM-1-Ligand in the sepsis patients is reported in FIG. 8. It is clearly evident that expression of TREM-1-Ligand drops in all sepsis patients at the time of recovery. The decrease of TREM-1-Ligand expression is observed in all septic patients analyzed, except in those two cases where a second sample was not made available because the patients died.

Figure 9:
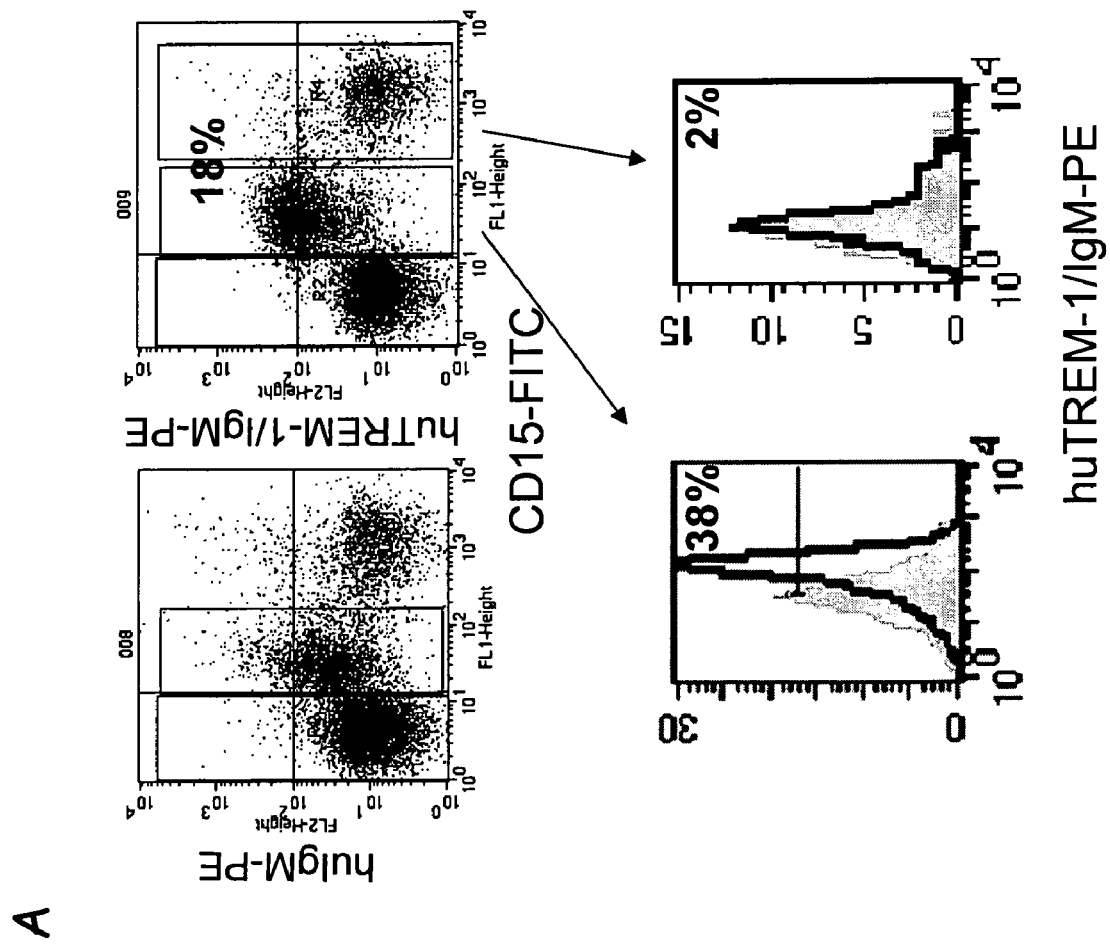
FIG. 9. shows TREM-1-Receptor and TREM-1-Ligand are expressed by different subsets of neutrophils in human sepsis and in the CLP mouse. Panel A) Expression of TREM-1-Ligand was evaluated on peripheral neutrophils of septic patients (peripheral pmn, sepsis patients) by double staining with anti human CD15 MAb and huTREM-1/IgM. Dot plots indicate that two different subsets of CD15 positive cells can be distinguished in septic patients: low CD15 and high CD15 expressing cells. The histogram plots indicate the percentages of TREM-1-Ligand expressing cells in the two subsets. The majority of TREM-1-Ligand expressing cells are found in the CD15 low subset (38%), while barely no cells are present in CD15 high subset. Panel B) Expression of TREM-1-Ligand was evaluated on peripheral neutrophils of CLP mice (CLP peritoneal lavage) by double staining with anti mouse Ly-6G and mTREM-1-Receptor/IgG. Dot plots indicate that two different subsets of Ly-6G positive cells can be distinguished in CLP mice: low Ly-6G and high Ly-6G expressing cells. The histogram plots indicate the percentages of TREM-1-Ligand expressing cells in the two subsets. The majority of TREM-1-Ligand expressing cells are found in the Ly-6G low subset (33%), while barely no cells are present in the Ly-6G high subset.

Notably, the expression of TREM-1-Ligand seems to be restricted to a subset of neutrophils during sepsis. As shown in FIG. 9, panel A, 38% of CD15 low neutrophils isolated from a septic patient expressed TREM-1-Ligand, while as few as 2% of CD15 high neutrophils expressed TREM-1-Ligand. The same pattern of TREM-1-Ligand expression is also detected on neutrophils from CLP mice (FIG. 10; panel B), where the majority of TREM-1-Ligand positive cells belong to the Ly-6G low subset of cells isolated from peritoneal lavage (77%), while only 33% of the Ly-6G high cells express TREM-1-Ligand.

In conclusion, the data presented here demonstrate that the expression of TREM-1-Ligand has a diagnostic value, since its expression is detected exclusively on circulating neutrophils from patients with SIRS of bacterial origin (sepsis) and not on neutrophils from patients with SIRS where bacterial infection could not be proven. Therefore, detection of TREM-1-Ligand expression permits early recognition of sepsis, an important issue in the management of the condition allowing earlier intervention.

In addition, the expression of TREM-1-Ligand has a prognostic value, because its expression on circulating neutrophils from patients with sepsis is completely down-regulated when the patients show clinical signs of recovery. Consequently, the monitoring of the expression of TREM-1-Ligand allows the follow-up of septic patients during the pharmacological treatment of the disease as well as assessment of current and novel therapies.

Example 3

Induction of TREM-1-Ligand Expression in vitro

Methods

In vitro Stimulation of Whole Blood with Crude Bacterial Extracts.

Bacteria isolated from blood cultures or bronchial exudates of septic patients were collected and crude extracts were prepared by repeating freezing and thawing. Total crude extracts were used for in vitro stimulation of whole blood. Briefly, whole blood was diluted 1:6 in complete RPMI medium. Crude bacterial extracts (1 µg/ml) were added directly to whole blood and incubated for 16 hours at 37/40° C. Staining with soluble TREM-1/IgM was performed as described above. Samples were analyzed by flow cytometry (FACS LSR, Becton Dickinson).

Results

Figure 10:
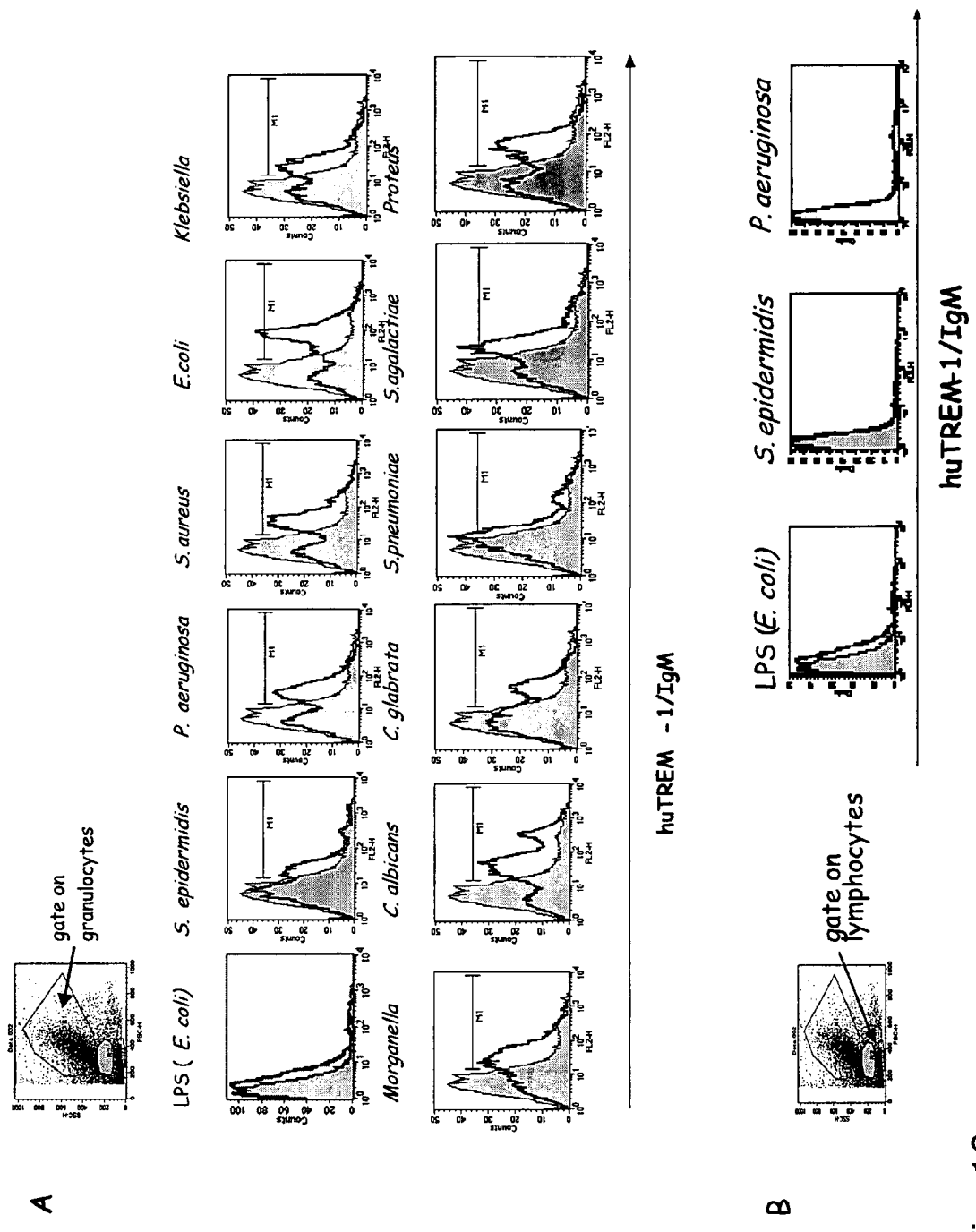
FIG. 10. shows in vitro induction of TREM-1-Ligand expression. In vitro stimulation of whole blood from healthy donor with total crude extracts of Gram-positive and Gram-negative bacteria from blood cultures of septic patients. Whole blood from a representative healthy donor was stimulated as described herein for 16 hours, cells were stained with huTREM-1-Receptor/IgM and analyzed by flow cytometry. Cells were gated based on physical parameters (SSC, side scatter and FSC, forward scatter). Histogram plots in panel A represent analysis of granulocytes (high SSC). Histogram plots in panel B represent analysis of lymphocytes (low SSC).

In order to analyze the time course of the expression of TREM-1-Ligand, we set up an in vitro system in which TREM-1-Ligand expression can be induced by defined stimuli. Whole blood from healthy donors was stimulated overnight with E.coli LPS or total crude bacterial extracts from Gram-positive bacteria, Gram-negative bacteria and fungi derived from blood cultures or bronchial exudates of septic patients. TREM-1-Ligand expression was evaluated by cytofluorimetric analysis on granulocytes and lymphocytes from peripheral blood. As shown in FIGS. 10 (panel A), expression of TREM-1-Ligand was induced on granulocytes by Gram$^+$, Gram$^-$ bacteria and fungi. TREM-1-Ligand expression is specifically induced on granulocytes, since its expression was not detected on peripheral lymphocytes stimulated under the same experimental conditions (FIG. 10, panel B) Addition of proinflammatory cytokines (TNFα, IL-1β, IL6, IL-12) during the stimulation only partially increased TREM-1-Ligand expression on granulocytes (data not shown). TREM-1-Ligand expression was detected as early as 2 hours after stimulation of whole blood with bacterial extracts and was detectable up to 16 hours after initial stimulation (data not shown). These data indicate that TREM-1-Ligand expression is promptly unregulated on the cell surface on neutrophils upon encounter with bacterial antigens in vitro.

Example 4

Figure 18:
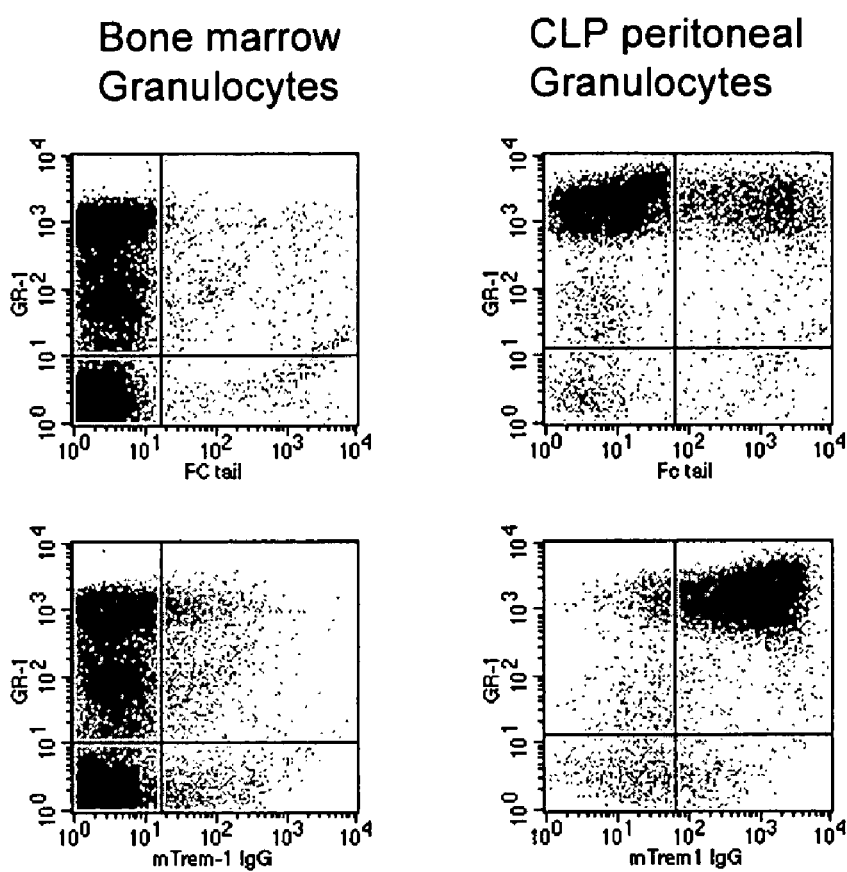
FIG. 18. shows immunofluorescence stainings performed with a TREM-1-tetramer construct. Briefly, Fc tail or mTrem1/IgG (mouse TREM-1/IgG Fc constant region fusion protein) are incubated with Protein A FITC at a molar ratio of 4:1 for 30 min at RT. The reactions are blocked with Human IgG for 15 min at RT. The complexes are transferred onto the samples and incubated for 1 hr on ice. Granulocytes are washed and counter-stained with anti GR-1 PE.

TREM-1 Ligand Identification: Generation of a Differential Expression Library of CLP Versus Normal Neutrophils TREM-1 ligand expression on murine neutrophils is tightly regulated: TREM-1 ligand is not present on peripheral neutrophils of normal mice or bone marrow derived mature granulocytes (FIG. 18).

TREM-1 ligand can be detected on neutrophils of the peritoneal cavity on CLP treated mice, with a peak of expression 5 hours after CLP induction. TREM-1 ligand can be identified among those genes that are differentially expressed between these two populations and followed by screening the gene for TREM-1 binding.

Generation of Subtracted cDNA Libraries.

Figure 19:
FIG. 19. shows the preparation of cDNA for subtraction. mRNA is isolated using Microfast-Track™ (Invitrogen).

Subtracted hybridization and suppressive PCR are performed using the PCR-select cDNA subtraction kit according to the manufacturers instructions (Clontech). This procedure combines subtractive hybridization and suppressive PCR in order to enrich for differentially expressed genes. Briefly, cDNA from the CLP versus normal mice are fragmented with Rsal, ligated with adaptors and then are subjected to alternate rounds of hybridization and PCR amplification. The subtraction protocol allows only molecules in the test population that did not hybridize with molecules in the control population to be exponentially amplified in subsequent cycles of PCR, resulting in a dramatic loss of common background sequences. As demonstrated by electrophoresis gel analysis (FIG. 19) the banding pattern of the subtracted population results in distinct bands rather than the smear produced by non subtracted cDNA. Furthermore, subtraction efficiency is confirmed by PCR to compare the abundance of the housekeeping gene β-actin in cDNA samples before and after subtraction (FIG. 20). The subtracted population is then cloned into a plasmid vector to generate a plasmidic library and plated in a 96 well plate format.

Differential Screening of Subtracted cDNA Clones.

Randomly selected clones, for example 400, are then screened to detect those differentially expressed in the TREM-1 Ligand positive population. Screening of the library is performed using $^{32}$P probes from un-subtracted or subtracted cDNA (FIG. 21).

Densitometry analysis allows the selection of clones that can be sequenced and compared to known sequences in public databases. The combined protocol of subtractive hybridization, suppressive PCR and differential screening is effective in removing commonly expressed genes. Many genes can be represented more than once among the subtracted clones. However, because of the nature of the subtraction procedure, the frequency with which clones matched a particular database entry is not an accurate reflection of expression levels for genes within the target population.

The differential gene expression observed can be validated using real-time PCR. Candidate gene(s) are then screened for TREM-1 binding by performing both in vitro transcription/translation and cytofluorimetric analysis on transfected cells as known in the art.

The invention claimed is:

1. A method of diagnosing bacterial or fungal sepsis in a subject, which method comprises the step of measuring the level of TREM-1-Ligand in a biological sample obtained from said subject.

2. The method of claim 1 wherein said step of measuring the level of TREM-1-Ligand comprises the steps of:
   (a) contacting said biological sample with a compound capable of binding TREM-1-Ligand;
   (b) detecting the level of TREM-1-Ligand present in the sample by observing the level of binding between said compound and TREM-1-Ligand.

3. The method of claim 2, comprising the further step of:
   c) correlating the detected level of TREM-1-Ligand with the presence or absence of bacterial or fungal sepsis.

4. The method of claim 3 where said correlation is made by comparing the measured level of TREM-1-Ligand in the sample with a mean level in a control sample or reference standard to indicate the presence or extent of bacterial or fungal sepsis in the patient.

5. The method of claim 2 wherein said compound specifically binds TREM-1-Ligand.

6. The method of claim 2 wherein said compound capable of binding TREM-1-Ligand is selected from the group consisting of:
   (a) a TREM-1 ligand binding fragment of SEQ ID NO: 2 or a homologue thereof;
   (b) a fusion protein comprising a bioactive molecule and one or more TREM-1 ligand binding domains of SEQ ID NO: 2 or a homologue thereof or a TREM-1 ligand binding fragment thereof;
   (c) a fusion protein comprising a detectable label and one or more TREM-1 ligand binding domains of SEQ ID NO: 2 or a homologue thereof or a TREM-1 ligand binding fragment thereof.

7. The method of claim 2 wherein said compound capable of binding TREM-1-Ligand is a TREM-1-Receptor/immunoglobulin fusion protein.

8. The method of claim 7 wherein said fusion protein comprises the sequence of FIG. 14 [SEQ ID NO: 4].

9. The method of claim 2 wherein said method is selected from the group consisting of a competitive immunoassay, western blots, a radioimmunoassay, an ELISA (enzyme linked immunosorbent assay), a "sandwich" immunoassay, an immunoprecipitation assay, a precipitin reaction, a gel diffusion precipitin reaction, an immunodiffusion assay, an agglutination assay, complement fixation assay, an immunoradiometric assay, a fluorescent immunoassay, a protein A immunoassay, an immunoprecipitation assay, an immunohistochemical assay, a competition or sandwich ELISA, a radioimmunoassay, a Western blot assay, an immunohistological assay, an immunocytochemical assay, a dot blot assay, a fluorescence polarization assay, a scintillation proximity assay, a homogeneous time resolved fluorescence assay, a IAsys analysis, and a BIAcore analysis.

10. The method of claim 1, further comprising the steps of measuring the level of TREM-1-Ligand in a second or further sample from the patient, the first and second or further samples being obtained at different times; and comparing the levels in the samples to indicate the progression or remission of the bacterial or fungal sepsis.

11. The method of claim 1 wherein said method is a method of diagnosing bacterial sepsis in a subject.

12. The method of claim 1 wherein the sample is selected from the group consisting of whole blood, blood serum, blood plasma, urine, cellular fractions of blood and neutrophils.

13. The method of claim 1 wherein the sample is a cell-free sample obtained from a biological fluid.

14. The method of claim 1 wherein the sample is a human sample.

15. A method of diagnosing bacterial or fungal sepsis in a subject which method comprises the step of measuring the binding of a TREM-1 receptor-derived polypeptide to a sample of neutrophils in a biological sample taken from a patient.

16. The method of claim 15, comprising the further step of correlating said binding with the presence or absence of bacterial or fungal sepsis.

17. The method of claim 16 where said correlation is made by comparing the measured level in a biological sample taken from a patient with a mean level in a control sample or reference standard to indicate the presence or extent of bacterial or fungal sepsis in the patient.

* * * * *

UNITED STATES PATENT AND TRADEMARK OFFICE
CERTIFICATE OF CORRECTION

| | | |
|---|---|---|
| PATENT NO. | : 7,534,571 B2 | Page 1 of 1 |
| APPLICATION NO. | : 10/548279 | |
| DATED | : May 19, 2009 | |
| INVENTOR(S) | : Margherita et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (184) days Delete the phrase "184 days" and insert -- by 433 days --

Signed and Sealed this

Thirty-first Day of August, 2010

David J. Kappos
*Director of the United States Patent and Trademark Office*

SEQUENCE LISTING

```
<160> NUMBER OF SEQ ID NOS: 11

<210> SEQ ID NO 1
<211> LENGTH: 884
<212> TYPE: DNA
<213> ORGANISM: Homo sapiens

<400> SEQUENCE: 1
ctactactac taaattcgcg gccggtcgac gctggtgcac aggaaggatg aggaagacca      60
ggctctgggg gctgctgtgg atgctctttg tctcagaact ccgagctgca actaaattaa     120
ctgaggaaaa gtatgaactg aaagaggggc agaccctgga tgtgaaatgt gactacacgc     180
tagagaagtt tgccagcagc cagaaagctt ggcagataat aagggacgga gagatgccca     240
agaccctggc atgcacagag aggccttcaa agaattccca tccagtccaa gtggggagga     300
tcatactaga agactaccat gatcatggtt tactgcgcgt ccgaatggtc aaccttcaag     360
tggaagattc tggactgtat cagtgtgtga tctaccagcc tcccaaggag cctcacatgc     420
tgttcgatcg catccgcttg gtggtgacca agggtttttc agggacccct ggctccaatg     480
agaattctac ccagaatgtg tataagattc ctcctaccac cactaaggcc ttgtgcccac     540
tctataccag ccccagaact gtgacccaag ctccacccaa gtcaactgcc gatgtctcca     600
ctcctgactc tgaaatcaac cttacaaatg tgacagatat catcagggtt ccggtgttca     660
acattgtcat tctcctggct ggtggattcc tgagtaagag cctggtcttc tctgtcctgt     720
ttgctgtcac gctgaggtca tttgtaccct aggcccacga acccacgaga atgtcctctg     780
acttccagcc acatccatct ggcagttgtg ccaagggagg agggaggagg taaaaggcag     840
ggagttaata acatgaatta aatctgtaat caccagctat ttct                      884

<210> SEQ ID NO 2
<211> LENGTH: 234
<212> TYPE: PRT
<213> ORGANISM: Homo sapiens

<400> SEQUENCE: 2
```

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
                35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230

<210> SEQ ID NO 3
<211> LENGTH: 16
<212> TYPE: PRT
<213> ORGANISM: Homo sapiens

<400> SEQUENCE: 3

Met Arg Lys Thr Arg Leu Trp Gly Leu Leu Trp Met Leu Phe Val Ser
1               5                   10                  15

<210> SEQ ID NO 4
<211> LENGTH: 184
<212> TYPE: PRT
<213> ORGANISM: Homo sapiens

<400> SEQUENCE: 4

Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
            20                  25                  30

Ala Ser Ser Gln Lys Ala Trp Gln Ile Ile Arg Asp Gly Glu Met Pro
        35                  40                  45

Lys Thr Leu Ala Cys Thr Glu Arg Pro Ser Lys Asn Ser His Pro Val
    50                  55                  60

Gln Val Gly Arg Ile Ile Leu Glu Asp Tyr His Asp His Gly Leu Leu
65                  70                  75                  80

-continued

```
Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
            100                 105                 110

Ile Arg Leu Val Val Thr Lys Gly Phe Ser Gly Thr Pro Gly Ser Asn
        115                 120                 125

Glu Asn Ser Thr Gln Asn Val Tyr Lys Ile Pro Pro Thr Thr Thr Lys
    130                 135                 140

Ala Leu Cys Pro Leu Tyr Thr Ser Pro Arg Thr Val Thr Gln Ala Pro
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg
            180

<210> SEQ ID NO 5
<211> LENGTH: 4
<212> TYPE: PRT
<213> ORGANISM: Homo sapiens

<400> SEQUENCE: 5

Asn Ser Thr Gln
1

<210> SEQ ID NO 6
<211> LENGTH: 4
<212> TYPE: PRT
<213> ORGANISM: Homo sapiens

<400> SEQUENCE: 6

Asn Leu Thr Asn
1

<210> SEQ ID NO 7
<211> LENGTH: 4
<212> TYPE: PRT
<213> ORGANISM: Homo sapiens

<400> SEQUENCE: 7

Asn Val Thr Asp
1

<210> SEQ ID NO 8
<211> LENGTH: 29
<212> TYPE: PRT
<213> ORGANISM: Homo sapiens

<400> SEQUENCE: 8

Val Pro Val Phe Asn Ile Val Ile Leu Leu Ala Gly Gly Phe Leu Ser
1               5                   10                  15

Lys Ser Leu Val Phe Ser Val Leu Phe Ala Val Thr Leu
            20                  25

<210> SEQ ID NO 9
<211> LENGTH: 5
<212> TYPE: PRT
<213> ORGANISM: Homo sapiens

<400> SEQUENCE: 9

Arg Ser Phe Val Pro
1               5
```

<210> SEQ ID NO 10
<211> LENGTH: 218
<212> TYPE: PRT
<213> ORGANISM: Homo sapiens

<400> SEQUENCE: 10

```
Glu Leu Arg Ala Ala Thr Lys Leu Thr Glu Glu Lys Tyr Glu Leu Lys
1               5                   10                  15
Glu Gly Gln Thr Leu Asp Val Lys Cys Asp Tyr Thr Leu Glu Lys Phe
            20                  25                  30
Ala Ser Ser Gln Lys Ala Trp Gln Ile Ile Arg Asp Gly Glu Met Pro
        35                  40                  45
Lys Thr Leu Ala Cys Thr Glu Arg Pro Ser Lys Asn Ser His Pro Val
    50                  55                  60
Gln Val Gly Arg Ile Ile Leu Glu Asp Tyr His Asp Gly Leu Leu
65                  70                  75                  80
Arg Val Arg Met Val Asn Leu Gln Val Glu Asp Ser Gly Leu Tyr Gln
                85                  90                  95
Cys Val Ile Tyr Gln Pro Pro Lys Glu Pro His Met Leu Phe Asp Arg
            100                 105                 110
Ile Arg Leu Val Val Thr Lys Gly Phe Ser Gly Thr Pro Gly Ser Asn
        115                 120                 125
Glu Asn Ser Thr Gln Asn Val Tyr Lys Ile Pro Pro Thr Thr Thr Lys
    130                 135                 140
Ala Leu Cys Pro Leu Tyr Thr Ser Pro Arg Thr Val Thr Gln Ala Pro
145                 150                 155                 160
Pro Lys Ser Thr Ala Asp Val Ser Thr Pro Asp Ser Glu Ile Asn Leu
                165                 170                 175
Thr Asn Val Thr Asp Ile Ile Arg Val Pro Val Phe Asn Ile Val Ile
            180                 185                 190
Leu Leu Ala Gly Gly Phe Leu Ser Lys Ser Leu Val Phe Ser Val Leu
        195                 200                 205
Phe Ala Val Thr Leu Arg Ser Phe Val Pro
    210                 215
```

<210> SEQ ID NO 11
<211> LENGTH: 990
<212> TYPE: DNA
<213> ORGANISM: Murine

<400> SEQUENCE: 11

```
gagcttgaag gatgaggaag gctgggctct ggggactgct gtgcgtgttc tttgtctcag      60
aagtcaaagc tgccattgtt ctagaggaag aaaggtatga cctagtggag ggccagactt     120
tgacagtgaa gtgtcccttc aacatcatga agtatgccaa cagccagaag gcttggcaga     180
gactaccaga cgggaaggaa cccttgaccc tggtggtcac acagaggccc tttacaagac     240
ccagtgaagt ccacatgggg aagttcaccc tgaaacatga ccctagtgag gccatgctac     300
aagttcaaat gactgacctt caagtgacag actctggatt gtatcgttgt gtgatttacc     360
atcctccgaa tgaccctgtt gtgctcttcc atcctgtccg cctggtggtg accaagggtt     420
cttcagatgt gttcactcct gtcatcattc ctattacaag gctgacagag cgtcccatcc     480
ttattaccac aaaatactca cccagtgaca aactacaac ccgatcccta cccaagccca     540
ctgcggtttt tcctctcct ggtcttggag tcactatcat aaatgggaca gatgctgaca     600
gtgtctccac atccagtgtt actatttcag tcatctgtgg acttctcagc aagagcctgg     660
```

-continued

```
ttttcatcat cttattcatt gtcacaaaga ggacatttgg atgacagaac ttgaagctat    720
acaatagtga ccttcagcgg tgtctatttc acaggaggag ctgaggtggt ggggctgagg    780
aggagctatg acatgaattg aacctgtaat caccggtgac gtctaaggct caggatatcc    840
tcagctgacc ctgtccactc tcctcatttt atccatcatc ttggggatgt gctctgcacc    900
cttagaaaag gggaaaccat tcccagaaca ctctggccat tccccctaaa tagttgggtt    960
ggcctgaaat aaagagaaac tccagagctt                                     990
```